United States Patent [19]

Dodd et al.

[11] Patent Number: 5,670,526
[45] Date of Patent: Sep. 23, 1997

[54] 1,3,4-OXADIAZOLES

[75] Inventors: Dharmpal S. Dodd, Germantown, Md.; Takao Nishi, Tokushima, Japan

[73] Assignee: Otsuka Pharmaceutical Co., Ltd., Osaka, Japan

[21] Appl. No.: 576,404

[22] Filed: Dec. 21, 1995

[51] Int. Cl.$^6$ .................. C07D 271/13; A61K 31/41
[52] U.S. Cl. .................. 514/340; 514/364; 546/176; 546/183; 546/256; 546/277; 548/131; 548/144
[58] Field of Search ................... 548/144, 131; 514/364, 340; 546/176, 183, 277, 256

[56] References Cited

U.S. PATENT DOCUMENTS 5,212,189  5/1993  Belliotti et al. .................... 514/363

FOREIGN PATENT DOCUMENTS

| | | |
|---|---|---|
| 177965A2 | 4/1986 | European Pat. Off. . |
| 449211A1 | 10/1991 | European Pat. Off. . |
| 488602A1 | 6/1992 | European Pat. Off. . |
| 533268A1 | 3/1993 | European Pat. Off. . |
| 542372A1 | 5/1993 | European Pat. Off. . |
| 57-64662 | 4/1982 | Japan . |
| 60-69075 | 4/1985 | Japan . |
| 62-39583 | 2/1987 | Japan . |
| 5750973 | 3/1992 | Japan . |
| 61135946 | 5/1994 | Japan . |

*Primary Examiner*—Robert Gerstl
*Attorney, Agent, or Firm*—Sughrue, Mion, Zinn, Macpeak & Seas

[57] ABSTRACT

1,3,4-oxadiazole compounds are disclosed. The subject compounds suppress immune function and have hepatoprotection activity.

13 Claims, No Drawings

1,3,4-OXADIAZOLES

FIELD OF THE INVENTION

The instant invention relates to novel 1,3,4-oxadiazoles, and salts thereof, which have a variety of activities including a dampening effect on immune reactivity and protection from liver injury. For example, the instant compounds inhibit the expression of cell adhesion molecules on endothelial cells and thus prevent the binding, for example, of neutrophils to the endothelium.

BACKGROUND OF THE INVENTION

Japan Laid-open Patent Publication (Kokai) No. JP-57/64662 discloses alkylenedithio derivatives and salts thereof:

wherein $R^1$ and $R^2$ are pyridyl, imidazolyl, pyrimidyl, 1,2,4-triazolyl, 1,3,4-oxadiazolyl, thiazolyl, 1,3,4-thiadiazolyl, benzimidazolyl or C(NH)—NHR$^3$, and the hetero ring may be substituted by 1 or 2 amino and/or lower alkyl groups; A is a lower alkylene group; $R^3$ is a lower alkyl group; and 1 and m are 0, 1 or 2. The compounds are asserted to be useful as anti-ulcer or anti-inflammatory agents.

Japan Laid-open Patent Publication (Kokai) No. JP-57/50973 discloses heterocyclic thiocarboxylic acids, esters and amides thereof and salts thereof:

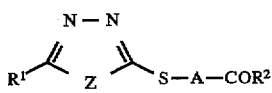

wherein $R^1$ is H, a lower alkyl group or an amino group; $R^2$ is a hydroxy, lower alkoxy or $NR^3R^4$ group; $R^3$ and $R^4$ are H, a lower alkyl or cycloalkyl group; A is a lower alkylene group; Z is O, S or N—$R^5$; and $R^5$ is H or a lower alkyl group. The compounds are asserted to be useful as antiinflammatory and antitumor agents.

Japan Laid-open Patent Publication (Kokai) No. JP-60/69075 discloses oxadiazole derivatives and salts thereof:

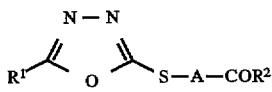

wherein $R^1$ is a lower alkyl group or a phenyl group; $R^2$ is a lower alkyl group or a cycloalkyl group; and A is a lower alkylene group. The compounds are asserted to be useful as ulcer-preventive and anti-inflammatory medicines.

Europe Patent Publication No. EP 488602 discloses aryl derivatives and salts thereof:

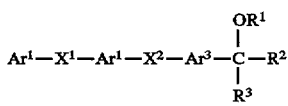

wherein $Ar^1$ is an optionally substituted phenyl or naphthyl group or a monocyclic or bicyclic heterocyclic moiety; $X^1$ is an oxy, thio, sulphinyl, sulphonyl, difluoromethylene, imino, (1–4C) alkylimino, optionally substituted (1–4C) alkylene group, —$X^4$—C(R)$_2$ or —C(R)$_2$—$X^4$— group, wherein $X^4$ is an oxy, thio, sulphinyl, sulphonyl or carbonyl moiety and each R is independently H, methyl or ethyl; each of $Ar^2$ and $Ar^3$ is an optionally substituted phenylene group; $X^2$ is an oxy, thio, sulphinyl or sulphonyl group; $R^1$ is a (1–4C) alkyl group, (3–4C) alkenyl group or a (3–4C) alkynyl group; and $R^2$ and $R^3$ together from a group of the formula —$A^1$—$X^3$—$A^2$— which together with the carbon atoms to which $A^1$ and $A^2$ are attached define a ring having 5 to 7 ring atoms, wherein each of $A^1$ and $A^2$ is a (1–3C) alkylene group and $X^3$ is an oxy, thio, sulphinyl or sulphonyl group. The compounds are asserted to be inhibitors of 5-lipoxygenase and useful in the treatment of allergic and inflammatory disease. The aryl derivatives do not relate to oxadiazoles as a 5-membered or 6-membered monocyclic group occurs at the $Ar^1$ position.

U.S. Pat. No. 5,212,189 discloses N-substituted phenylaniline derivatives and salts thereof:

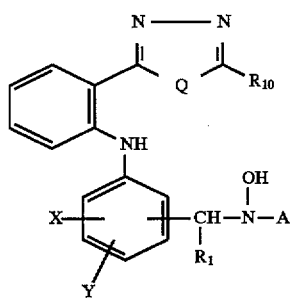

wherein $R_{10}$ is OH, SH or $NH_2$; $R_1$ is H or a lower alkyl group; X and Y each is H, halo, lower alkyl, lower alkoxy, $CF_3$ or OH; A is CW—Z; W is O or S; Z is a lower alkyl, lower alkoxy or $NR_2R_3$ group; Q can be O or S and $R_2$ and $R_3$ each is H or a lower alkyl group. The compounds are believed to be inhibitors of 5-lipoxygenase and/or cyclooxygenase and useful for treating and preventing inflammation, rheumatoid arthritis, pain, fever, osteoarthritis etc.

Europe Patent Publication No. EP 533268 discloses benzanilide derivatives and salts thereof:

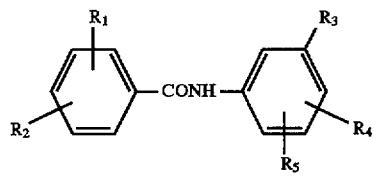

wherein $R_1$ is H, halo, (1–6C) alkyl or (1–6C) alkoxy; $R_2$ is phenyl (i) substituted by a group of formula (a)–(f) and (ii) optionally monosubstituted or disubstituted by halo, (1–6C) alkoxy, OH or (1–6C) alkyl;

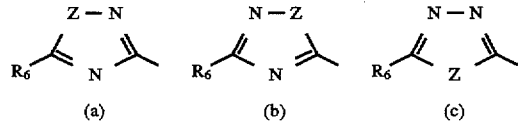

5,670,526

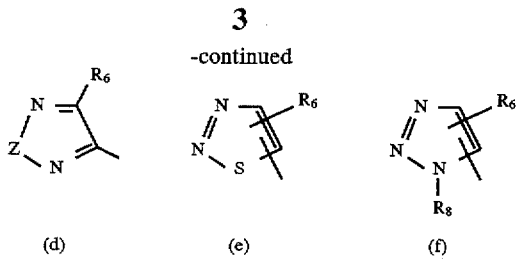

(d)     (e)     (f)

$R_3$ is a 4-$R_7$-1-piperazinyl group; $R_4$ and $R_5$ each is H, halo, OH, (1–6C) alkoxy or (1–6C) alkyl; $R_6$ is H, $NR_9R_{10}$ or (1–6C) alkyl (optionally mono-substituted or di-substituted with (1–6C) alkoxy, OH, (1–6C) acyloxy or $SO_2R_{11}$); $R_{7-9}$ each is H or (1–6C) alkyl; $R_{10}$ is H, (1–6C) alkyl, (1–6C) acyl, benzoyl or $SO_2R_{11}$; $R_{11}$ is a (1–6C) alkyl or phenyl group; Z is O, $NR_8$ or $S(O)_k$; and k is 0–2. Those compounds are believed to be useful as 5-hydroxytryptamine antagonists for treating depression, anxiety, panic, dementia, Parkinson's disease and hypertension.

Europe Patent Publication No. EP 449211 discloses 2,6-di-t-butylphenol derivatives:

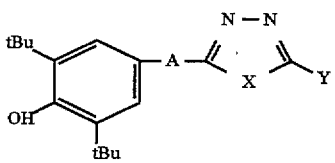

wherein A is CO, C=NOH, $S(O)_n(CH_2)_m$, $(CH_2)_m$, $S(O)_n$, $CO(CH_2)_m$, O or $O(CH_2)_m$; X is O or S; Y is H, OH, SH, $NH_2$, NH—CN, NH—C(NH)—NHR, SMe, SOMe or $SO_2Me$; R is H or (1–6C) alkyl; n is 0–2; and m is 1–2, provided that when A is $(CH_2)_2$ and Y is OH then X is not O. The compounds are believed to be useful as inhibitors of 5-lipoxygenase or cyclooxygenase and for treating inflammatory diseases.

Europe Patent Publication No. EP 177965 discloses oxadiazole or thiadiazole derivatives:

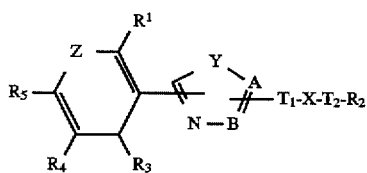

wherein one of A and B is N and the other is C; $T_1$ is a lower alkylene or alkenylene (optionally interrupted by a phenylene group) group or a single bond; $T_2$ is CO, a lower alkylene (optionally substituted by an aryl group) group or a single bond; X is $NR_6$, piperazine-1,4-diyl, S, SO or $SO_2$; Y is O or S; Z is $NR_7$ or O; $R_6$ is H, lower alkyl, cycloalkyl or aralkyl; $R_7$ is H or lower alkyl; one of $R_1$ and $R_5$ is a lower alkyl, alkenyl or haloalkyl group and the other is a lower alkyl, alkenyl, haloalkyl, hydroxyalkyl, alkoxyalkyl, alkanoyloxyalkyl, dialkoxyalkyl, CHO, CN or $NH_2$ group; $R_2$ is an aryl, aryloxy, a 5-membered or 6-membered unsaturated heterocyclic, cycloalkyl or adamantyl group, or $R_2$ and $R_6$ may complete a 5-membered to 8-membered saturated ring optionally containing o-phenylene and/or is substituted by a lower alkyl, oxo, aryl, arakyl or aroyl group; $R_3$ is an aryl, pyridyl (optionally in the N-oxide form), thienyl, furyl, 2,1,3-benzoxadiazolyl, lower alkyl, cycloalkyl, aralkyl or benzhydryl group, the rings being optionally substituted by 1 or 2 of halogen, $NO_2$, $CF_3$, CN, lower alkyl, lower alkoxy, polyfluoroalkoxy and benzyloxy; and $R_4$ is H, CN, $CONH_2$, lower alkanoyl, $COOR_8$ or a group of the formula:

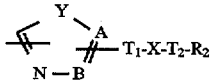

wherein $R_8$ is a saturated or unsaturated (1–10C) hydrocarbyl, $T_3R_9$ or $T_3NR_{10}R_{11}$ group, $T_3$ is a lower alkylene group, $R_9$ is a lower alkoxy, cycloalkyl, CN, polyfluoroalkyl, aryl or pyridyl group, and $R_{10}$ and $R_{11}$ each is a lower alkyl group. The compounds are Ca antagonists and vasodilators asserted to be useful for treating cardiovascular disorders.

SUMMARY OF THE INVENTION

The instant invention relates to 1,3,4-oxadiazole derivatives:

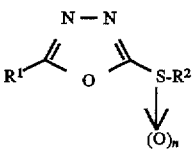

wherein $R^1$ is an alkyl group, a phenyl group, optionally having a lower alkoxy group, a hydroxy group, a lower alkyl group, optionally having a halogen substituent, a halogen atom or an anilino group, optionally substituted on the phenyl ring thereof with 1–3 optionally halogen-substituted lower alkyl groups or halogens, an adamantyl group, a naphthyl group, a phenyl(lower)alkyl group, optionally having a phenoxy group on the phenyl ring or an unsaturated 5-membered to 11-membered heteromonocyclic or heterobicyclic group having 1–4 heteroatoms selected from the group consisting of a nitrogen, an oxygen and a sulfur, said heterocyclic group being optionally substituted with a phenyl group, a phenoxy group or a lower alkyl group; $R^2$ is a phenyl group, optionally having 1–3 lower alkyl groups or hydroxyl groups, a phenyl(lower)alkyl group,

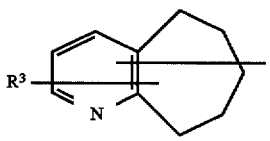

wherein $R^3$ is a hydrogen atom, a lower alkoxy group, a quinolyl group or a lower alkyl group substituted with an unsaturated 5-membered to 11-membered heteromonocyclic or heterobicyclic group having 1 to 4 heteroatoms selected from the group consisting of a nitrogen, an oxygen and a sulfur atom, said heterocyclic group being optionally substituted with a phenyl group, optionally having a lower alkyl substituent on the phenyl ring, a phenyl(lower)alkyl group, a lower alkoxy group, an oxo group, a lower alkyl group or a phenoxy group; and n is 0 or 1.

DETAILED DESCRIPTION OF THE INVENTION

The oxadiazoles of the instant invention have a profound effect on the immune system. The instant compounds temper the immune response. While it is unclear how the instant compounds achieve that effect, the local, isolated activity of the instant compounds is manifest by way of an effect on specific effector functions. Hence, the instant compounds, among other activities, can inhibit the expression of cell adhesion molecules on endothelial cells and thus inhibit neutrophil binding thereto and the transendothelial migration thereof, can inhibit cytokine production and can protect hepatocytes against agents known to be hepatotoxic and thus protect against liver injury.

The compounds of the instant invention may be used for modulating immunoreactivity, inhibiting and/or reducing the production of cytokines and inhibiting and/or reducing the expression of cell adhesion molecules on endothelial cells. Thus, the instant compounds are useful in part as anti-inflammatory agents, anti-allergy agents, cytokine production inhibitory agents and cell adhesion molecule expression inhibitory agents.

The instant compounds can be administered to a host, such as any animal of commercial and personal interest, including domestic animals, pets, other mammals, zoo specimens including other vertebrates and the like to obtain the desired therapeutic effects.

The compounds of the instant invention are oxadiazole derivatives that can be synthesized using known techniques with known and available starting materials. The instant compounds may contain one or more asymmetric carbon atoms and may exist in racemic and optically active forms. All of those compounds are contemplated to be within the scope of the instant invention.

The various modifications to the procedures contemplated to be required to obtain the specific compounds of interest are standard and known in the art and an artisan will be able to call on a variety of art-recognized organic synthesis schemes and methodologies to make a compound of interest.

The starting acid hydrazide can be purchased from commercial sources or can be prepared either by heating the appropriate methyl or ethyl esters with hydrazine in refluxing alcohol or by reacting the appropriate acid chlorides with hydrazine in $CH_2Cl_2$.

The 1,3,4-oxadiazole-2-thiols can be prepared by condensing the $R^1$-containing acid hydrazides with $CS_2$ in the presence of a base, such as, powdered KOH, powdered NaOH, $K_2CO_3$, $Na_2CO_3$ or hindered tertiary alkyl amines in, preferably, alcoholic solvents such as, EtOH, MeOH, isopropyl alcohol etc. The cyclized oxadiazoles can be isolated either as salts or acidified using concentrated hydrochloric acid to give the thiols. For example, using KOH as the base in the cyclization reaction results in the isolation of the potassium salt of the 1,3,4-oxadiazole. The preparation of 2-mercapto-1,3,4-oxadiazoles and acid hydrazines is described in U.S. Pat. No. 5,212,189, EP-449211, JP-57/64662 and JP-57/50973.

The thioethers of the instant invention can be prepared by directly coupling the potassium salts of the appropriate 1,3,4-oxadiazole-2-thiols with $R^2$—(X), where X may be a bromine, chlorine, iodine, tosyloxy, mesityloxy or other sulfonyloxy group in acetone, dimethylformamide (DMF) or alcohol solvents. Alternatively, the reaction can be conducted by reacting the appropriate 1,3,4-oxadiazole-2-thiols with $R^2$—(X), where X is as described above, in the presence of a base, such as $K_2CO_3$, KOH or triethylamine, or other hindered trialkyl amines, in solvents such as, acetone, dimethylformamide or alcohols. The $R^2$—(X) moiety used in the instant invention either is obtained from commercial sources or prepared according to standard protocols. Relevant literature for the preparation of 2-(1,3,4-oxadiazolyl) thioethers include JP-57/64662 and JP-57/50973. The thioethers then are treated with limiting amounts of 3-metachloroperoxybenzoic acid to yield the sulfoxide compounds of interest.

The various modifications for making the compounds of interest are known. For example, when the $R^2$—(X) group is 4-bromo-3,5-ditertbutylphenol, a typical coupling reaction requires heating the appropriate 1,3,4-oxadiazole-2-thiol potassium salt with 4-bromo-3,5-ditertbutylphenol in dimethylformamide (DMF) at about 110° C. for several hours. When $R^2$ is 2,6-dimethylbenzene as in 2-(2,6-dimethylphenyl)sulfinyl-5-methyl-1,3,4-oxadiazole, the modification to the usual protocol requires displacement of the methylsulfinyl group of 2-methylsulfinyl-5-methyl-1,3, 4-oxadiazole with the thiolate anion of 2,6-dimethylthiophenol to give 2-(2,6-dimethylphenyl)thio-5-methyl-1,3,4-oxadiazole.

A typical procedure for synthesizing the 1,3,4-oxadiazoles of the instant invention is described below.

For example, in one variation, a methyl or ethyl ester is dissolved in a suitable volume of alcohol in a round bottom flask and stirred at room temperature. Then hydrazine is added at room temperature and the flask is fitted with a condenser and refluxed for about 12–24 hours. The solvent is removed under vacuum and the resulting oily solid is chromatographed with a solvent, such as, ethyl acetate and hexane in 1:1 to 8:2 ratios, to yield the acid hydrazide.

In another method, the appropriate acid chloride is dissolved in a suitable volume of methylene chloride ($CH_2Cl_2$) and then cooled in an ice bath. To the stirring solution hydrazine is added dropwise by a syringe. The reaction is stirred at 0° and then at room temperature. The solvent is removed in vacuo and the resulting material is resuspended in a suitable volume of alcohol. The solution is made basic with, for example, solid $K_2CO_3$, the solids are removed by filtration and the filtrate condensed in vacuo. The hydrazide was purified further by silica gel chromatography using, for example, ethyl acetate and hexane as a solvent or recrystallized from appropriate solvent mixtures.

$CS_2$ is added dropwise to a mixture of the acid hydrazide and powdered KOH in alcohol in a round bottom flask. The resulting slurry is stirred at room temperature and then the flask is fitted with the reflux condenser and the mixture refluxed for about 24 hours. Alcohol and excess $CS_2$ are removed in vacuo and the resulting potassium salt is rinsed with a mixture of $CH_2Cl_2$-EtOH to remove the soluble contaminants.

The thiol is prepared by resuspending the potassium salt in alcohol and acidifying to pH 2–3 with concentrated hydrochloric acid. The precipitate is filtered, the filtrate concentrated in vacuo and the 1,3,4-oxadiazole-2-thiol is purified further using silica gel chromatography with a solvent comprising, for example, ethyl acetate and hexane or MeOH and $CH_2Cl_2$ as eluants. When the oxadiazole-2-thiols are isolated as potassium salts, the purification involves recrystallization from protic solvents.

To the 1,3,4-oxadiazole-2-thiol and $K_2CO_3$ in acetone is added the $R^2$—Y—(X) reagent. The mixture is stirred for 12–24 hours at room temperature. The reaction is diluted with water and extracted with ether. The ether extracts are combined and washed with saturated NaCl solution, dried over $MgSO_4$ and the solvent is removed in vacuo to give a product usually 95% pure by NMR. The coupled thioether is purified further by chromatography over silica gel using a solvent comprising, for example, ethyl acetate and hexanes. The thioether then is dissolved in an appropriate amount of $CH_2Cl_2$ in a round bottom flask and treated with a slight excess of metachloroperoxybenzoic acid (m-CPBA) at ice bath temperature for 3–5 hours. Excess m-CPBA is neutralized using aqueous $Na_2S_2O_3$ solution. Standard work-up procedures described above give the oxidized 1,3,4-oxadiazole-2-sulfinyl product of interest contaminated with other side products. The active compounds can be isolated in pure form by chromatography on silica gel using combinations of ethyl acetate and hexanes as the eluant.

By those very methods and those exemplified in the examples hereinbelow, representative compounds of the invention are provided in the working examples and tables hereinbelow.

The 1,3,4-oxadiazoles of the instant invention are represented by the following formula:

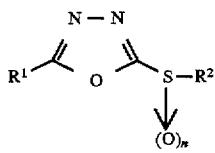

wherein $R^1$ is an alkyl group, a phenyl group, optionally having a lower alkoxy group, a hydroxy group, a lower alkyl group, optionally having a halogen substituent, a halogen atom or an anilino group, optionally substituted on the phenyl ring thereof with 1–3 lower alkyl groups, optionally having a halogen substituent, or halogen atoms, an adamantyl group, a naphthyl group, a phenyl(lower)alkyl group, optionally having a phenoxy group on the phenyl ring, or an unsaturated 5-membered to 11-membered heteromonocyclic or heterobicyclic group having 1–4 heteroatoms selected from the group consisting of a nitrogen, an oxygen and a sulfur, said heterocyclic group being optionally substituted with a phenyl group, a phenoxy group or a lower alkyl group; $R^2$ is a phenyl group optionally having 1–3 lower alkyl groups or hydroxyl groups, a phenyl (lower) alkyl group,

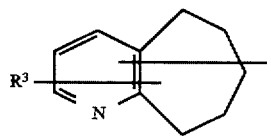

wherein $R^3$ is a hydrogen atom, a lower alkoxy group, a quinolyl group or a lower alkyl group substituted with an unsaturated 5-membered to 11-membered heteromonocyclic or heterobicyclic group having 1–4 heteroatoms selected from the group consisting of a nitrogen, an oxygen and a sulfur atom, said heterocyclic group being optionally substituted with a phenyl group, optionally having a lower alkyl substituent on the phenyl ring, a phenyl(lower)alkyl group, a lower alkoxy group, an oxo group, a lower alkyl group or a phenoxy group; and n is 0 or 1.

Particular compounds of interest are those where $R^1$ is not a 4H-pyranyl group or a 1,4-dihydropyridyl group; when $R^1$ is a lower alkyl group or phenyl group, $R^2$ is not a pyrazyl-substituted lower alkyl group having a lower alkyl group, a lower alkoxy group or an oxo group as a substituent; and where $R^2$ is not a 1,1,3-trioxo-1,2-benzisothiazolylmethyl group.

Regarding the various groups of the above general formula, the following exemplary species are preferred.

The alkyl group includes $C_{1-10}$ straight-chained or branched-chained alkyl groups, such as methyl, ethyl, propyl, isopropyl, butyl, isobutyl, tertbutyl, pentyl, hexyl, heptyl, octyl, nonyl and decyl groups.

The lower alkoxy group includes $C_{1-6}$ straight-chained or branched-chained alkoxy groups, such as methoxy, ethoxy, propoxy, isopropoxy, butoxy, tertbutoxy, pentyloxy and hexyloxy groups.

The lower alkyl group optionally having a halogen substituent includes $C_{1-6}$ straight-chained or branched-chained alkyl groups optionally having 1–3 halogen atoms, such as methyl, ethyl, propyl, isopropyl, butyl, isobutyl, tertbutyl, pentyl, hexyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-bromopropyl, 3-chloropropyl, 2,3-dichloropropyl, 4,4,4-trichlorobutyl, 4-fluorobutyl, 5-chloropentyl, 3-chloro-2-methylpropyl, 5-bromohexyl and 5,6-dichlorohexyl groups.

The anilino group optionally substituted on the phenyl ring by 1–3 lower alkyl groups, optionally having a halogen substituent, or halogen atoms includes those containing on the phenyl ring C1–6 straight-chained or branched-chained alkyl groups, optionally having 1–3 halogen atoms, or halogen atoms, such as anilino, 2-methylanilino, 3-methylanilino, 4-methylanilino, 2-ethylanilino, 3-propylanilino, 4-butylanilino, 2-pentylanilino, 3-hexylanilino, 2,3-dimethylanilino, 3,4,5-trimethylanilino, 2-(iodomethyl)anilino, 3-trifluoromethylanilino, 4-trichloromethylanilino, 2-(2,2,2-trifluoroethyl)anilino, 3-(3-bromopropyl)anilino, 4-(4,4,4-trichlorobutyl)anilino, 2-(5-chloropentyl)-anilino, 3-(5-bromohexyl)anilino, 2-methyl-3-trifluoromethylanilino, 2-chloroanilino, 3-chloroanilino, 4-chloroanilino, 2-fluoroanilino, 3-fluoroanilino, 4-fluoroanilino, 2-bromoanilino, 3-bromoanilino, 4-bromoanilino, 2-iodoanilino, 3-iodoanilino, 4-iodoanilino, 3,4-dichloroanilino, 6-dichloroanilino, 2,3-dichloroanilino, 2,4-dichloroanilino, 3,4-difluoroanilino, 3,5-dibromoanilino, 3,4,5-trichloroanilino, 2,3,6-trimethylanilino and 3-methyl-2-chloroanilino groups.

The halogen atom includes fluorine, chlorine, bromine and iodine.

The phenyl group optionally having a lower alkoxy group, a hydroxy group, a lower alkyl group, optionally having a halogen substituent, a halogen atom or an anilino group, optionally substituted on the phenyl ring by 1–3 lower alkyl groups, optionally having a halogen substituent, or halogen atoms includes a phenyl group optionally having 1–3 $C_{1-6}$ straight-chained or branched-chained alkoxy groups, hydroxy groups, $C_{1-6}$ straight-chained or branched-chain alkyl groups, optionally having 1–3 halogen atomes, halogen atoms or anilino groups, optionally substituted on the phenyl ring by 1–3 $C_{1-6}$ straight-chained or branched-chained alkyl groups, optionally having 1–3 halogen atoms, or halogen atoms, such as phenyl, 2-methoxyphenyl, 3-methoxyphenyl, 4-methoxyphenyl, 2-ethoxyphenyl, 3-propoxyphenyl, 4-butoxyphenyl, 2-pentoxyphenyl, 3-hexoxyphenyl, 2,4-dimethoxyphenyl, 3,4-diethoxyphenyl, 3,4,5-trimethoxyphenyl, 2-(3-trifluoromethylanilino)phenyl, 3-anilinophenyl, 2-(2,3-dimethylanilino)phenyl, 2-(2,6-dichloro-3-methylanilino) phenyl, 4-methoxy-3-anilinophenyl, 4-(2-bromoanilino) phenyl, 2-(4,4,4-trichlorobutylanilino)phenyl, 3-(4-chloroanilino)phenyl, 2-hydroxy phenyl, 3-hydroxy phenyl, 4-hydroxy phenyl, 2,3-dihydroxy phenyl, 2,4,6-trihydroxy phenyl, 3-trifluoromethyl phenyl, 4-trifluoromethyl phenyl, 4-fluorophenyl, 2-chlorophenyl, 3-bromophenyl, 3-fluorophenyl, 2,6-dichloro-4-methylphenyl, 3-methylphenyl, 2,3-dimethyl phenyl, 2,4,6-trimethylphenyl and 2-(2,6-dichloroanilino)phenyl groups.

The phenyl(lower)alkyl group, optionally having a phenoxy group on the phenyl ring, includes phenyl(lower)alkyl groups having a $C_{1-6}$ straight-chained or branched-chained alkyl group as the alkyl moiety and optionally having 1–3 phenoxy groups as substituents on the phenyl ring, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-phenoxybenzyl, 2-(3-phenoxyphenyl)ethyl, 1-(3-phenoxyphenyl)ethyl, 3-(2-phenoxyphenyl)propyl, 4-(3-phenoxyphenyl)butyl, 5-(4-phenoxyphenyl)pentyl, 1,1-dimethyl-2-(2-phenoxyphenyl) ethyl, 6-(3-phenoxyphenyl)hexyl, 3,4-diphenoxybenzyl, 3,5-diphenoxybenzyl, 2,6-diphenoxybenzyl, 2,3-diphenoxybenzyl, 2,4-diphenoxybenzyl, 3,4-diphenoxybenzyl, 3,5-diphenoxybenzyl and 3,4,5-triphenoxybenzyl groups.

The unsaturated 5-membered to 11-membered heteromonocyclic or heterobicyclic group having 1–4 heteroatoms selected from a nitrogen, an oxygen or a sulfur atom includes pyridyl, 1,2,5,6-tetrahydropyridyl, thienyl, quinolyl, 1,4-dihydroquinolyl, benzothiazolyl, pyrazyl, pyrimidyl, pyridazyl, pyrrolyl, carbostyril, 3,4-dihydrocarbostyril, 1,2,3,4-tetrahydroquinolyl, indolyl, isoindolyl, indolinyl, benzimidazolyl, benzoxazolyl, isoquinolyl, quinazolidinyl, 1,2,3,4-tetrahydroquinolyl, 1,2-dihydroisoquinolyl, 1,2,3,4-tetrahydroisoquinolyl, quinoxalinyl, cinnolinyl, phthalazinyl, 1,2,3,4-tetrazolyl, 1,2,4-triazolyl, 1,2,4-oxadiazolyl, chromanyl, isoindolinyl, isochromanyl, pyrazolyl, imidazolyl, pyrazolidinyl, imidazo[1,2-a]pyridyl, benzofuryl, 2,3-dihydrobenzo[b]furyl, benzothienyl, 4H-chromenyl, 1H-indazolyl, isoindolinyl, 2-imidazolinyl, 2-pyrrolinyl, furyl, oxazolyl, isooxazolyl, thiazolyl, isothiazolyl, pyranyl, 2-pyrazolinyl, quinuclidinyl, 1,4-benzoxazinyl, 3,4-diydro-2H-1,4-benzoxazinyl, 3,4-dihydro-2H-1,4-benzothiazinyl, 1,4-benzothiazinyl, 1,2,3,4-tetrahydroquinoquisalinyl, 1,3-dithia-2,4-dihydronaphthalenyl and 1,4-dithianaphthalenyl groups.

The above-mentioned heterocyclic group may have a substituent selected from the group consisting of a phenyl group, a phenoxy group and a lower alkyl group. The substituted heterocyclic group includes the above-mentioned heterocyclic groups having 1–3 substituents selected from the group consisting of a phenyl group, a phenoxy group and a $C_{1-6}$ straight-chained or branched-chained alkyl group, such as 1-phenoxy-1,2,3,4-tetrahydroisoquinolyl, 5-phenylthiazolyl, 1-methylimidazolyl, 1-propylimidazolyl, 4-methylimidazolyl, 4-phenylimidazolyl, 1,4-dimethylpyrrolyl, 4-methylthiazolyl, 2-phenoxythiazolyl, 5-ethylthiazolyl, 4-phenylthiazolyl, 4-propylthiazolyl, 5-butylthiazolyl, 4-pentylthiazolyl, 2-hexylthiazolyl, 4,5-dimethylthiazolyl, 5-phenyl-4-methylthiazolyl, 1-ethylimidazolyl, 4-propylimidazolyl, 5-butylimidazolyl, 1-pentylimidazolyl, 1-hexylimidazolyl, 1,4-dimethylimidazolyl, 1,4,5-trimethylimidazolyl, 1-phenylimidazolyl, 2-phenylimidazolyl, 5-phenylimidazolyl, 1-methyl-4-phenylimidazolyl, 3-methyl-1,2,4-triazolyl, 5-ethyl-1,2,4-triazolyl, 3-phenyl-1,2,4-triazolyl, 2-phenoxy-1-methylimidazolyl, 2-phenoxyimidazolyl, 2-ethylpyrrolyl, 1-methylpyrrolyl, 3-propylpyrrolyl, 5-butylpyrrolyl, 4-pentylpyrrolyl, 2-hexylpyrrolyl, 2,4,5-trimethylpyrrolyl, 2-phenylpyrrolyl, 2,5-diphenylpyrrolyl, 2-methyl-5-phenylpyrrolyl, 2-phenoxypyrrolyl, 1-methyl-1,2,3,4-tetrazolyl, 1-phenyl-1,2,3,4-tetrazolyl, 1-ethyl-1,2,3,4-tetrazolyl, 1-propyl-1,2,3,4-tetrazolyl, 1-butyl-1,2,3,4-tetrazolyl, 1-pentyl-1,2,3,4-tetrazolyl, 1-hexyl-1,2,3,4-tetrazolyl, 2-methylpyridyl, 3-ethylpyridyl, 4-propylpyridyl, 2-butylpyridyl, 3-pentylpyridyl, 4-hexylpyridyl, 2-phenylpyridyl, 3-phenylpyridyl, 4-phenylpyridyl, 2,4-dimethylpyridyl, 2,4,6-trimethylpyridyl, 2-methyl-4-phenylpyridyl, 2,4-diphenylpyridyl, 2,4,6-triphenylpyridyl, 2-phenoxypyridyl, 4-phenoxypyridyl, 4-methyl-2-phenoxypyridyl, 2-phenyl-4-phenoxypyridyl, 3-methylimidazo[1,2-a]pyridyl, 4-ethylimidazo[1,2-a]pyridyl, 3-phenylimidazo[1,2-a]pyridyl, 5-phenylimidazo[1,2-a]pyridyl, 3-methyl-1H-indazolyl, 3-phenyl-1H-indazolyl, 1-methyl-1,2,3,4-tetrahydroisoquinolyl, 5-ethyl-1,2,3,4-tetrahydroisoquinolyl, 2-phenylquinolyl, 6-phenyl-1,2,3,4-tetrahydroisoquinolyl, 1-phenoxy-6-methyl-1,2,3,4-tetrahydroisoquinolyl and 1-phenoxy-7-phenyl-1,2,3,4-tetrahydroisoquinolyl groups.

The lower alkyl group includes $C_{1-6}$ straight-chained or branched-chained alkyl groups, such as methyl, ethyl, propyl, isopropyl, butyl, isobutyl, tertbutyl, pentyl and hexyl groups.

The phenyl group, optionally having 1–3 lower alkyl groups or hydroxyl groups, includes a phenyl group, optionally having 1–3 $C_{1-6}$ straight-chained or branched-chained alkyl groups or hydroxyl groups, such as phenyl, 2-methylphenyl, 3-methylphenyl, 4-methylphenyl, 2-ethylphenyl, 3-propylphenyl, 4-butylphenyl, 2-pentylphenyl, 3-hexylphenyl, 2,6-dimethylphenyl, 3,4,5-trimethylphenyl, 4-hydroxyphenyl, 3-hydroxyphenyl, 2-hydroxyphenyl, 2,4-dihydroxyphenyl, 2,4,6-trihydroxyphenyl and 4-hydroxy-3,5-di-t-butylphenyl groups.

The phenyl(lower)alkyl group includes a $C_{1-6}$ straight-chained or branched-chained alkyl group having 1 or 2 phenyl groups, such as benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl, diphenylmethyl and 2,2-diphenylethyl groups.

The phenyl group, optionally having a lower alkyl substituent on the phenyl ring, includes phenyl groups which may have 1–3 $C_{1-6}$ straight-chained or branched-chained alkyl groups bound thereto, such as phenyl, 2-methylphenyl, 3-methylphenyl, 4-methylpenyl, 2-ethylphenyl, 3-propylphenyl, 4-butylphenyl, 2-pentylphenyl, 3-hexylphenyl, 3,4-dimethylphenyl and 3,4,5-trimethylphenyl groups.

The lower alkyl group substituted by an unsaturated 5-membered to 11-membered heteromonocyclic or heterobicyclic group having 1–4 heteroatoms selected from a nitrogen, an oxygen or a sulfur atom includes $C_{1-6}$ straight-chained or branched-chained alkyl groups substituted by the above-mentioned unsaturated 5-membered to 11-membered heteromonocyclic or heterobicyclic groups having one or more heteroatoms.

The above-mentioned heterocycle-substituted lower alkyl group may further have a substituent selected from the group consisting of a phenyl group, optionally having a lower alkyl substituent on the phenyl ring, a phenyl(lower)alkyl group, a lower alkoxy group, an oxo group, a lower alkyl group and a phenoxy group. The heterocycle-substituted lower alkyl group optionally having a substituent includes $C_{1-6}$ straight-chained or branched-chained alkyl groups substituted by the above-mentioned heterocyclic group having 1–3 substituents selected from the group consisting of a phenyl group, optionally having 1–3 $C_{1-6}$ straight-chained or branched-chained alkyl groups, a $C_{1-6}$ straight-chained or branched-chained alkyl group having 1 or 2 phenyl groups, a $C_{1-6}$ straight-chained or branched-chained alkoxy group, an oxo group, a $C_{1-6}$ straight-chained or branched-chained alkyl group and a phenoxy group, such as (3,5-dimethyl-4- methoxy-2-pyridyl)methyl, (2-pyridyl)methyl, [3-(4-t-butylphenyl)-1,2,4-oxadiazol-5-yl]methyl, (1-benzyl-2-imidazolyl)methyl, (2-benzimidazolyl)methyl, (1-benzyl-2-benzimidazolyl)methyl, (1-oxo-2-pyridyl)methyl, (1-oxo-3,5-dimethyl-4-methoxy-2-pyridyl)methyl, (1-benzyl-5-methyl-4-imidazolyl)methyl, (3-phenoxy-2-pyridyl)methyl, 2-(1-phenoxy-1,2,3,4-tetrahydroisoquinolyl-3-yl)ethyl, 1-(5-phenyl-2-thiazolyl)ethyl, 3-(1-methyl-4-imidazolyl)propyl, 4-(1-propyl-5-imidazolyl)butyl, 5-(4-methyl-1-imidazolyl)pentyl, 6-(4-phenyl-1-imidazolyl)hexyl, (1,4-dimethyl-1-pyrrolyl)methyl, 2-(4-methyl-2-thiazolyl)ethyl, 1-(2-phenoxy-4-thiazolyl)ethyl, 3-(5-ethyl-2-thiazolyl)propyl, 4-[4-(4-methylphenyl)-2-thiazolyl]butyl, 5-(5-phenyl-4-methyl-2-thiazolyl)pentyl, 6-(1-ethyl-2-imidazolyl)hexyl, (4-methoxy-2-imidazolyl)methyl, 2-(5-ethoxy-2-imidazolyl)ethyl, 1-(1-phenyl-2-imidazolyl)ethyl, 3-(1,4-dimethyl-5-imidazolyl)propyl, 4-(1,4,5-trimethyl-2-imidazolyl)butyl, 1-diphenylmethyl-2-imidazolyl)methyl, 5-(5-phenoxy-1-imidazolyl)pentyl, 6-[2-(2,4,6-trimethylphenyl)-1-imidazolyl]hexyl, (1-methyl-4-phenyl-2-imidazolyl)methyl, 2-(3-methyl-1,2,4-triazol-1-yl)ethyl, 1-(3-phenyl-1,2,4-triazol-1-yl)ethyl, (1-methyl-3-pyrrolyl)methyl, 3-(2-methyl-5-phenyl-1-pyrrolyl)propyl, (1-methyl-1,2,3,4-tetrazol-5-yl)methyl, 2-(1-phenyl-1,2,3,4-tetrazol-5-yl)ethyl, (2-methylpyridyl)methyl, 2-(3-ethyl-2-pyridyl)ethyl, 1-(4-propyl-2-pyridyl)ethyl, 3-(2-butyl-4-pyridyl)propyl, 4-(3-pentyloxy-5-pyridyl)butyl, 5-(4-hexyloxy-2-pyridyl)pentyl, 6-(2-phenoxy-3-pyridyl)hexyl, [3-(4-pentylphenyl)-2-pyridyl]methyl, (4-benzyl-2-pyridyl)methyl, (2,4-dimethyl-3-pyridyl)methyl, (2,4,6-trimethyl-5-pyridyl)methyl, [2-methyl-4-(2-phenylethyl)-6-pyridyl]methyl, (2,4-benzyl-3-pyridyl)methyl, (4-phenoxy-2-pyridyl)methyl, 2-(4-methoxy-2-phenoxy-3-pyridyl)ethyl, 3-(4-methyl-2-propoxy-5-pyridyl)propyl, 2-(2-phenyl-4-ethoxy-6-pyridyl)ethyl, (3-methylimidazo[1,2-a]pyridin-2-yl)methyl, 2-(4-ethylimidazo[1,2-a]pyridin-3-yl)ethyl, (3-methyl-1H-indazol-1-yl)methyl, 2-(3-phenyl-1H-indazol-4-yl)ethyl, (1-methyl-1,2,3,4-tetrahydroisoquinolin-3-yl)methyl, 1-(5-ethoxy-1,2,3,4-tetrahydroisoquinolin-6-yl)ethyl, (2-phenylquinolin-6-yl)methyl, (6-phenoxy-1,2,3,4-tetrahydroisoquinolin-7-yl)methyl, (1-benzyl-7-methoxy-1,2,3,4-tetrahydroisoquinolin-6-yl)methyl, 1-oxo-1,2,3,4-tetrahydroisoquinolyl, 2-oxothiazolyl, 2-oxo-1-methylimidazolyl, 2-oxoimidazolyl, 2-oxopyrrolyl, 4-oxopyridyl, 4-methyl-2-oxopyridyl, 2-phenyl-4-oxopyridyl and 1-oxo-6-methyl-1,2,3,4-tetrahydroisoquinolyl groups.

Preferred compounds include those wherein $R^1$ is an alkyl group; or those wherein $R^2$ is a phenyl(lower)alkyl group. Those preferred substituents may coexist in the same compound.

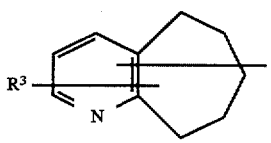

Other preferred compounds are those wherein $R^2$ is wherein $R^3$ is a hydrogen or a lower alkoxy group, a quinolyl group, a lower alkyl group substituted by an unsaturated 5-membered to 11-membered heteromonocyclic or heterobicyclic group having 1–4 heteroatoms selected from a nitrogen, an oxygen or a sulfur atom, said heterocyclic group being optionally substituted by a phenyl group, optionally having a lower alkyl substituent on the phenyl ring, a phenyl(lower)alkyl group, a lower alkoxy group, an oxo group, a lower alkyl group or a phenoxy group, or a phenyl group optionally having 1–3 lower alkyl groups or hydroxyl groups or a quinolyl group.

Other preferred compounds are those wherein $R^1$ is an unsaturated 5-membered to 11-membered heteromonocyclic or heterobicyclic group having 1–4 heteroatoms selected from the group consisting of a nitrogen, an oxygen and a sulfur atom, said heterocyclic group being optionally substituted by a phenyl group, a phenoxy group or a lower alkyl group, and R2 is a phenyl(lower)alkyl group; or when $R^1$ is a phenyl group, optionally having a lower alkoxy group or an anilino group, optionally substituted on the phenyl ring by 1–3 lower alkyl groups, optionally having a halogen substituent, or halogen atoms, an adamantyl group, a naphthyl group or a phenyl(lower)alkyl group optionally having a phenoxy group as a substituent on the phenyl ring.

For example, a preferred compound is (3,5-dimethyl-4-methoxy-2-pyridyl)methylsulfinyl-5-methyl-1,3,4-oxadiazole.

Further details on the synthesis of the compounds of interest from known and available starting materials are known to the artisan and representative examples thereof are provided hereinbelow.

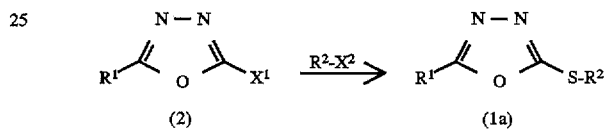

Starting materials (2) and $R^2$—$X^2$ are reacted to form compound (1a), wherein $R^1$ and $R^2$ are as defined above, and $X^1$ and $X^2$ each is a mercapto group, —SM (wherein M is an alkali metal), a halogen atom, a lower alkanesulfonyloxy group, an arylsulfonyloxy group or an aralkylsulfonyloxy group, with the proviso that when $X^1$ is a mercapto group or —SM, $X^2$ is a halogen atom, a lower alkanesulfonyloxy group, an arylsulfonyloxy group or an aralkylsulfonyloxy group, and when $X^2$ is a mercapto group or —SM, $X^1$ is a halogen atom, a lower alkanesulfonyloxy group, an arylsulfonyloxy group or an aralkylsulfonyloxy group. Examples of the alkali metal represented by M in the above formula include sodium, potassium and lithium.

In compounds (2) and $R^2$—$X^2$, the halogen atom represented by $X^1$ and/or $X^2$ is as defined above; examples of the lower alkanesulfonyloxy group include methanesulfonyloxy, ethanesulfonyloxy, isopropanesulfonyloxy, propanesulfonyloxy, butanesulfonyloxy, tertbutanesulfonyloxy, pentanesulfonyloxy, hexanesulfonyloxy and the like; examples of the arylsulfonyloxy group include a substituted or unsubstituted arylsulfonyloxy group such as phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy, 24-naphthylsulfonyloxy and the like; and examples of the aralkylsulfonyloxy group include a substituted or unsubstituted aralkylsulfonyloxy group, such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, 24-naphthylmethylsulfonyloxy and the like.

The reaction between compound (2) and $R^2$—$X^2$ can be carried out in a suitable solvent in the presence of a basic compound. Any solvent which does not affect the reaction adversely can be used as the solvent. Examples of the solvent include water; alcohols, such as methanol, ethanol, isopropanol etc.; aromatic hydrocarbons, such as benzene, toluene, xylene etc.; ethers, such as diethyl ether, tetrahydrofuran, dioxane, monoglyme, diglyme etc.; ketones, such as acetone etc.; esters, such as methyl acetate, ethyl acetate etc.; aprotic polar solvents, such as N,N-dimethyl formamide (DMF), dimethylsulfoxide (DMSO), hexamethyl phosphoric triamide (HMPA) etc.; or a mixed solvent thereof.

Examples of the basic compound which can be used include inorganic bases, such as sodium hydride, sodium hydroxide, potassium hydroxide, sodium carbonate, potassium carbonate, sodium hydrogencarbonate, potassium hydrogencarbonate, silver carbonate etc.; alkali metals, such as metal sodium, metal potassium etc.; alcoholates, such as sodium methylate, sodium ethylate etc.; and organic bases such as triethylamine, pyridine, N,N-dimethylaminopyridine, N-methylmorpholine, 1,5-diazabicyclo[4.3.0]nonene-5 (DBN), 1,8-diazabicyclo[5.4.0]undecen-7 (DBU), 1,4-diazabicyclo[2.2.2]octane (DABCO) etc.

The reaction proceeds advantageously with the addition of a crown ether, such as 18-crown-6 (1,4,7,10,13,16-hexaoxacyclooctadecane), 15-crown-5 (1,4,7,10,13-pentaoxacyclopentadecane), 12-crown-4 (1,4,7,10-tetraoxacyclododecane) and the like.

The reaction is carried out usually at 0° C. to 150° C., preferably at about 0° C. to 120° C., and completed in about 1 to 30 hours. Compound (2) usually is used in an amount of at least 1 mole, preferably 1–12 moles, per mole of $R^2—X^2$.

using known techniques, wherein $R^1$ and $R^2$ are as defined above.

The oxidation reaction of compound (1a) can be carried out in a suitable solvent in the presence of an oxidizing agent. Any solvent which does not affect the reaction adversely can be used as the solvent. Examples of the solvent include water; organic acids, such as formic acid, acetic acid, trifluoroacetic acid etc.; alcohols, such as methanol, ethanol, isopropanol etc.; and halogenated hydrocarbons, such as chloroform, dichloromethane, dichloroethane etc.

Any oxidizing agent that usually oxidizes a sulfide group to a sulfoxide group can be used as the oxidizing agent. Examples of the oxidizing agent include peroxy acids, such as performic acid, peracetic acid, trifluoroperacetic acid, perbenzoic acid, m-chloroperbenzoic acid, o-carboxyperbenzoic acid etc.; hydrogen peroxide; chromic acid; chromates, such as sodium chromate, potassium chromate etc.; permanganic acid; permanganates, such as sodium permanganate, potassium permanganate etc; iodates, such as sodium metaperiodate etc.; and seleniums, such as selenium dioxide etc.

The oxidizing agent is used in an amount of at least 1 mole, preferably 1–1.5 moles, per mole of compound (1a). The reaction is carried out usually at –70° C. to 40° C., preferably at about –70° C. to room temperature and completed in about 5 minutes to 3 hours.

When the heterocyclic group represented by $R^1$ or $R^2$ has at least one heteroatom selected from a tertiary amine and a sulfur atom, the tertiary amine or the sulfur atom might be oxidized to form an N-oxide or sulfoxide compound. Those compounds, however, can be separated easily.

Alternatively, compounds (4) and (5), wherein $R^1$ and $R^2$ are as defined above, and $R^4$ is a lower alkyl group, can be reacted to form compound (1a).

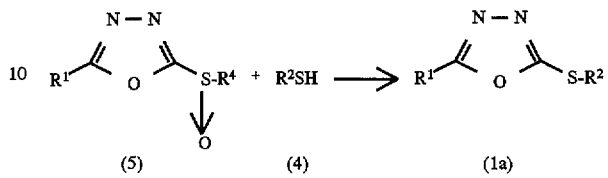

The reaction between compound (5) and compound (4) can be carried out under conditions similar to those of the reaction between compound (2) and compound (3) described hereinabove. Compound (4) usually is used in an amount of at least 1 mole, preferably 1–2 moles, per mole of compound (5).

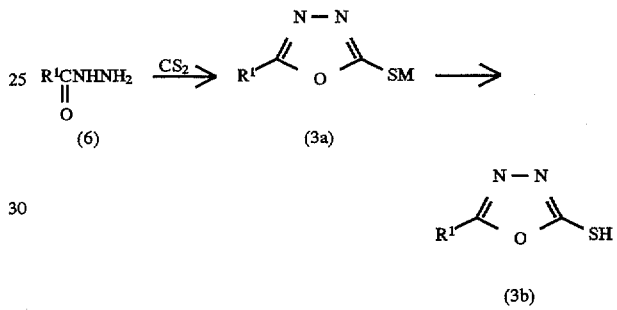

The reaction between compound (6) and $CS_2$, wherein $R^1$ and M are as defined above, can be carried out in a suitable solvent in the presence of a basic compound. Examples of the solvent include water; alcohols, such as methanol, ethanol, isopropanol etc.; aromatic hydrocarbons, such as benzene, toluene, xylene etc.; ethers, such as diethyl ether, tetrahydrofuran, dioxane, monoglyme, diglyme etc.; ketones, such as acetone etc.; esters, such as methyl acetate, ethyl acetate etc.; aprotic polar solvents, such as DMF, DMSO, HMPA etc.; or a mixed solvent thereof.

Examples of the basic compound include inorganic bases, such as sodium hydride, sodium hydroxide, potassium hydroxide, sodium carbonate, potassium carbonate, sodium hydrogencarbonate, potassium hydrogencarbonate, silver carbonate and the like; alkali metals, such as metal sodium, metal potassium and the like; and alcoholates, such as sodium methylate, sodium ethylate and the like.

The reaction usually is carried out at room temperature to 150° C., preferably at room temperature to about 100° C. and completed in about 1 to 30 hours. $CS_2$ usually is used in an amount of 1–10 moles, preferably 1–5 moles, per mole of compound (6).

Compound (3a) can be converted to compound (3b) by reacting compound (3a) with a mineral acid, such as hydrochloric acid, sulfuric acid or hydrobromic acid in a solvent such as those as used in the reaction between compound (6) and $CS_2$. Then, compound (3b), as a representative of compound (2), is reacted with $R^2—X^2$ to yield a compound of interest. An example of a suitable $R^2—X^2$ compound is one of formula (10).

Some compounds of formula (10) can be produced according to the process shown below.

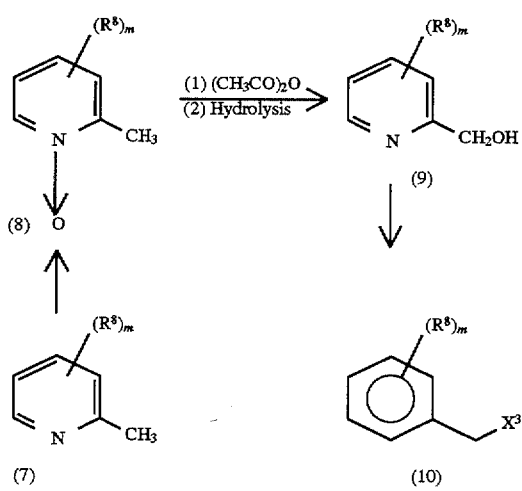

wherein R⁸ is a phenyl group, optionally having a lower alkyl substituent on the phenyl ring, a phenyl (lower)alkyl group, a lower alkoxy group, an oxo group, a lower alkyl group or a phenoxy group, m is 0 or an integer of 1–3, and when m is 2 or 3, R⁸ may be the same or different, and X³ is a halogen.

The conversion reaction of compound (7) to compound (8) can be carried out in a suitable solvent in the presence of an oxidizing agent. The solvent and oxidizing agent which can be used include all the examples mentioned above in the conversion reaction of compound (1a) to compound (1b). The oxidizing agent is used in an amount of at least 1 mole, preferably 1–5 moles, per mole of compound (7). The reaction usually is carried out at room temperature to 150° C., preferably at room temperature to about 120° C., and completed in about 1–15 hours.

The conversion reaction of compound (8) to compound (9) can be carried out in acetic anhydride usually at room temperature to 150° C., preferably at room temperature to about 120° C. for about 1–5 hours. The intermediate O-acetate that is generated can be hydrolyzed to (9) by treatment with alkoxide bases, such as aqueous potassium hydroxide, sodium hydroxide, sodium methoxide etc. Alternatively, acidic hydrolysis using aqueous HCl, aqueous sulfuric acid etc. with heating up to 100° C. can be practiced.

Any of the conventional reaction conditions for halogenation of hydroxyl groups can be applied to the halogenation reaction of compound (9) to (10). The halogenation reaction can be carried out, for example, by reacting compound (9) with a halogenating agent in a suitable inert solvent or without a solvent. Examples of the halogenating agent which can be used include hydrogen halides such as hydrochloric acid, hydrobromic acid etc.; phosphorous pentachloride, thionylchloride etc. Examples of the inert solvent which can be used include ethers, such as dioxane, tetrahydrofuran etc.; and halogenating hydrocarbons, such as chloroform, methylene chloride, carbon tetrachloride etc. The halogenating agent is used at least in an equimolar proportion, usually in an excess proportion, relative to compound (9). The reaction is carried out usually at 0° C. to 150° C., preferably at 0° C. to 80° C., and completed in about 10 minutes to 6 hours.

Among the compounds of the instant invention, those compounds having acidic groups can be converted to pharmaceutically acceptable salts by reaction with a basic compound. Examples of the basic compounds include metal hydroxides, such as sodium hydroxide, potassium hydroxide, lithium hydroxide, calcium hydroxide etc., alkali metal carbonates or alkali metal hydrogen carbonates, such as sodium carbonates, sodium hydrogen carbonate etc., and alkali metal alcoholates, such as sodium methylate, potassium ethylate etc. Compounds of the instant invention having basic groups can be converted to pharmaceutically acceptable salts by permitting a conventional acid to act therewith. Examples of acids include inorganic acids, such as sulfuric acid, nitric acid, hydrochloric acid, hydrobromic acid etc., and organic acids, such as acetic acid, p-toluenesulfonic acid, ethanesulfonic acid, oxalic acid, maleic acid, fumaric acid, citric acid, succinic acid, benzoic acid etc.

The instant invention contemplates the use of those salts, as well as free compounds, stereoisomers and optical isomers thereof as active ingredient compounds in various compositions.

The desired compounds obtained by the processes described herein can be separated from the reaction systems by conventional means for separation and then further purified. Useful separation means and purification means are, for example, distillation, recrystallization, column chromatography, ion exchange chromatography, gel chromatography, affinity chromatography, preparative thin layer chromatography and the like.

The compounds of the instant invention affect the immune system of a host. The various activities of the instant molecules can be assessed by a variety of correlative in vitro assays. For example, inflammation arises from an accumulation of for example, lymphocytes, at a body site and the lymphocytes can release any of a variety of effector molecules, such as cytokines, that have a variety of physiologic effects. Localization of lymphocytes at a site can be mediated by antibody and can occur by cell-cell interactions. Thus, an assay for lymphocyte presence or effector molecule presence can result in an inference that an inflammatory state may exist in situ.

Cytokines relate to a group of proteins or glycoproteins which act through cell surface receptors to serve as regulators of immune responses. Cytokines also are known as or include lymphokines, monokines, interleukins and interferons and are produced by a wide variety of cells in animals. Cytokines are known to play an important role in many physiologic responses, such as in immune responses and inflammation, where the cytokines can regulate the amplitude and duration of response.

Cytokines are a diverse group of molecules with sometimes overlapping regulatory activity. The cytokines often interact in a network resulting in synergistic, additive or antagonistic interactions on cell function. Balkwill et al. disclose the cytokine network and the multiple activities and functions of the cytokines (Balkwill et al., Immunology Today, 10(9): 299–303, 1989). The cytokines include interferon-α, interferon-β, interferon-γ, tumor necrosis factor (TNF), lymphotoxin (LT), interleukin-1 (IL-1), including IL-1α and IL-1β, interleukin-2 (IL-2), interleukin-1 (IL-3), interleukin-4 (IL-4), interleukin-5 (IL-5), interleukin-6 (IL-6), interleukin-7 (IL-7), interleukin-8 (IL-8), macrophage colony-stimulating factor (M-CSF), glanulocyte colony-stimulating factor (G-CSF), glanulocyte/macrophage colony-stimulating factor (GM-CSF) and various growth factors.

PCT Application WO93/07141 discloses heterocyclic 3-phenylpyrrolidin-2-ones asserted to be useful as a medicament for inhibiting TNF production. TNF-associated diseases include rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to acquired immune deficiency syndrome (AIDS), ARC (AIDS-related complex), keloid formation, scar tissue formation, Crohn's disease, ulcerative colitis and yeast and fungal infections.

Acute allergic reactions in the skin and airways are often followed by a more sustained inflammatory reaction characterized by the appearance of eosinophils and basophils, as well as neutrophils and mononuclear cells. The cytokines, such as IL-1 and TNF, can stimulate cultured endothelial cells to acquire adhesive properties for various peripheral blood leukocytes in vitro.

It is believed, based on work by several laboratories in the past decade, that the binding of leucocytes to the vascular wall, a process that can be mimicked in vitro with IL-1 treatment of endothelial cells, is a first step in the diapedesis of leucocytes into tissue space. However, several aspects of that process, especially as related to the utility of current anti-inflammatory agents for intervention, remain unclear.

IL-1 induces a rapid alteration in the membrane properties of cultured human endothelial cells. That is evident from the ability of treated cells to bind leucocytes, the acquisition of procoagulant activity and the expression of new cell surface antigens including some for which no functional property has yet been assigned. In those cases studied, the development of the new properties described is sensitive to the action of actinomycin D and cycloheximide, suggesting a requirement for the synthesis of new message and new proteins.

Binding of leucocytes and tumor cells of hematopoietic origin to basal and activated endothelial cells as well as to the "high" endothelial cells of capillaries has been studied by several laboratories. Evidence has been presented that granulocytes, monocytes, T-cells and B-cells all can bind to endothelial cells after stimulation with physiologic concentrations of IL-1 (Bevilacqua et al., J. Clin. Invest., 76: 2003–2011, 1985; Cavender et al., J. Immunol., 136: 203–207, 1986; Pohlman et al., J. Immunol., 136: 4548–4553, 1986).

T-cell binding also can be induced by pretreatment of endothelial cells with IFN-gamma (Yu et al., Clin. Exp. Imm., 62: 554–560, 1985; Masuyama & Kano, J. Clin. Invest., 77: 1596–1605, 1986), IL-1 (Cavender et al., J. Immunol., 136: 203–207, 1986; Bender et al., J. Clin. Invest., 79: 1679–1688, 1987), lps (Yu et al., J. Immunol., 136: 569–573, 1986) and TNF (Cavender et al., J. Immunol, 139: 1855–1860, 1987).

The pro-adhesive effects of those cytokines for quiescent endothelium is viewed as a model of early events in the extravasatory component of inflammation. In the case of high endothelial venules (HEV), the constituent endothelial cells presumably are activated already in some manner which facilitates the role thereof in the recirculation of T-cells and B-cells (reviewed in: Yednock et al., Adv. in Immunol., 44: 313–378, 1989). The binding of monocytes (Pawlowski et al., J. Exp. Med., 168: 1865–1882, 1988; Wallis et al., J. Immunol., 135: 2323–2330, 1985) and granulocytes (Lo et al., J. Exp. Med., 169: 1779–1793, 1989) to cultured endothelial cells which otherwise are not stimulated has been taken as a model for the margination of those cell types within the circulatory system.

A fundamental assumption of research into lymphocyte recirculation and the early stages of inflammation is the existence of selective mechanisms for the binding and extravasation of leucocyte subsets. The existence of such mechanisms is inferred from the differential recirculation of lymphocytes through mucosal versus peripheral lymphoid organs (reviewed in: Yednock et al., Adv. in Immunol., 44: 313–378, 1989), the kinetic difference in the extravasation of neutrophils, monocytes and lymphocytes in inflammation (Issekutz et al., Am. J. Pathol., 103: 47, 1981) and the selective binding and accumulation of monocytes in atherogenesis (Taylor & Lewis, Am. J. Pathol., 125: 152, 1986).

T-cells are late but persistent elements of inflammatory lesions, especially those which continue in chronic form. The role of T-cells in the pathogenesis of autoimmune diseases (Wofsy & Seaman, J. Exp. Med., 161: 378–391, 1985; Ranges et al., J. Exp. Med., 162: 1105–1110, 1985; Taurog et al., Cell. Immunol., 75: 271–282, 1983; Maron et al., J. Immunol., 131: 2316–2322, 1983; Rossini et al., Ann. Rev. Immunol., 3: 289–320, 1985) has led to interest in the emigration thereof to sites of eventual tissue damage with special emphasis on the interaction thereof with activated or pro-adhesive endothelial elements.

Direct and indirect evidence strongly suggests that the adhesion of leucocytes to basal or activated endothelial cells is a complex process. While four apparently distinct structures have been described on activated endothelial cells (Hagemeier et al., Int. J. Cancer, 38: 481–488, 1986; Goerdt et al., Expl. Cell. Biol., 55: 117–126, 1987; Duijvestijin et al., Am. J. Pathol., 130: 147–155, 1988; Leeuwenberg et al., Eur. J. Immunol., 19: 715–720, 1989), at least two additional well characterized molecules have been implicated directly in adhesion events.

The adhesion molecules include ELAM-1 (endothelial leukocyte adhesion molecule-1) or E-selection, VCAM-1 (vascular cell adhesion molecule-1) and ICAM-1 (intercellular adhesion molecule-1). VCAM-1 and ICAM-1 are molecules of the immunoglobulin superfamily having immunoglobulin-like domains with the characteristic disulfide bonds. ELAM-1 has a C-type lectin-like domain. ELAM-1, VCAM-1 and ICAM-1 are about 95 kD to 110 kD in molecular weight. It is suggested that the local expression of ELAM-1, VCAM-1 and ICAM-1 may contribute to the recruitment of basophils, eosinophils and neutrophils during experimental allergic reactions and in chronic allergic diseases (Bochner et al., J. Exp. Med., 173: 1553–1556, 1991).

It is suggested that the regulation of ELAM-1 expression controls acute inflammatory responses and thus could have a role in affecting airway function associated with inflammatory disorders, including asthma (Gundel et al., J. Clin. Invest., 88: 1407–1411, 1991). Furthermore, Silber et al. suggested that both VCAM-1 and E-selectin are functionally relevant in the genesis of cutaneous DHR, and each molecule appears to contribute to lymphocyte recruitment (Silber et al., J. Clin. Invest., 93: 1554–1563, 1994).

The ELAM-1 protein appears to mediate primarily the adhesion of granulocytes to cytokine-activated endothelium (Pober et al., J. Immunol., 136: 1680–1687, 1986; Bevilacqua et al., Proc. Natl. Acad. Sci., 84: 9238–9242, 1987; Science, 243: 1160–1165, 1989); and the ICAM-1 protein partially is responsible for the adhesion of some mononuclear cells (Dustin & Springer, J. Cell Biol., 107: 321–331, 1988) and granulocytes (Smith et al., J. Clin. Invest., 83: 2008–2017, 1989; Smith et al., J. Clin. Invest., 82: 1746–1756, 1988) to activated endothelial cells. A significant point of agreement (Haskard et al., J. Imm., 137: 2901–2906, 1986) is on the existence of ICAM-1 and ELAM-1 independent pathway(s) for the adherence of lymphocytes to activated endothelial cells.

Hence, the cytokines, such as TNF, IL-1, GM-CSF and INF-γ, and the adhesion molecules, such as ELAM-1 and VCAM-1, are related with disease caused or mediated by the immune system and the improper function thereof.

The following terms are used herein according to the following definitions.

The phrase "inflammatory responses associated with activated endothelial cells" as applied to the novel compounds of the instant invention, means inflammatory responses characterized by the participation of endothelial cells, and the blood vessels wherein they reside, in the stable binding and/or extravasation of leucocytes from the blood stream into the tissues. Inflammation might consist in binding only, if that leads to leucocyte-mediated damage to the local vasculature. Damage also may result from actual passage through the blood vessel resulting in the damage to surrounding tissues from interaction with any of the different leucocyte subtypes.

"ELAM" is one of a family of endothelial cell surface molecules with the characteristics of a lectin-like domain at the N-terminus and a carbohydrate binding ligand. The family is called selectins. ELAM also is one of the E-selectins.

"VCAM" is one or a family of endothelial cell surface molecules.

"ICAM" is a member of the immunoglobulin supergene family. It is a ligand for integrin molecules on leucocyte cell surfaces.

"ELAM ligand" is one or more cell surface molecules on cells of the immune system that enables attachment of immune cells to endothelial cells by binding to ELAM on the endothelial cells.

"VCAM ligand" is one or more cell surface molecules on cells of the immune system that enables attachment of immune cells to endothelial cells by binding to VCAM on the endothelial cells. An example is VLA-4.

"ICAM ligand" is one or more cell surface molecules on cells of the immune system that enables attachment of immune cells to endothelial cells by binding to ICAM on the endothelial cells. An example is LFA-1.

The phrase "biological fluid" means serum, urine, synovial fluid and any other body fluid expected to contain evidence of immune system status, such as sites of inflammation.

In general, several known methods can be used for demonstrating the effect of the instant compounds on the immune system, such as those described in, for example, Handbook of Experimental Immunology, 4th Edition, 1986, Weir, editor, Vols. 1–4, Blackwell Scientific Publications, Oxford, England; Masuyama & Kano, J. Clin. Invest., 77: 1596–1605, 1986; and Pober et al., J. Immunol., 136: 1680–1687, 1986. The artisan is directed to the many references cited herein for a catalog of a variety of techniques which may not be taught explicitly in the instant application and which can be used to assess the activity of the instant compounds on the host and the immune system thereof.

For example, detection of the effects of the instant compounds on the immune system or on a specific element of the immune system can occur either in vitro or in vivo. In vitro testing can provide valid prediction of the state of the immune system in situ.

In vitro detection can be carried out using any of the known in vitro immunological assays, such as those described by Young et al., J. Exp. Med., 150: 1008–1019, 1979 and Kannagi et al., Cancer Res., 43: 4997–5005, 1983. Further, in vivo, detection can be carried out using any of the known immunological assays, such as those described in Burchell et al., Int. J. Cancer, 34: 763–768, 1984; Epenetos et al., Lancet, 2: 999–1004, 1982; Chatal et al., J. Nuclear Med., 26: 531–537, 1985.

An especially preferred method for the detection of antigen in biological fluids is an ELISA, such as a sandwich ELISA. That method in preferred form consists of the attachment of monoclonal antibodies to one epitope of the target of interest to a plastic multiwell dish. That is followed by adding a blocking agent in about a 1% solution to block non-specific binding of molecules in biological fluids. After rinsing wells to remove unbound proteins, the biological fluids are added (blood, urine etc.) to the dish for an incubation. After washing to remove unbound biological fluid, the second monoclonal antibody to the same or to another epitope of the target of interest is added. The second monoclonal antibody is conjugated with a suitable reporter molecule, such as alkaline phosphatase. After a period of incubation, the wells are washed to remove unbound antibody and a suitable enzyme substrate (if the reporter molecule is an enzyme), such as aminoethyl carbazole, is added and the amount of reaction product is quantitated on an ELISA plate reader. An example of conducting a sandwich ELISA is described in Lokeshwar & Lin, J. Immunol. Methods, 123: 123–129, 1989). Polyclonal antibodies also can be used in the procedures.

The physiologic manifestations of the instant compounds can be monitored or exemplified in any known techniques for assessing immune function, such as lymphocyte accumulation, delayed-type hypersensitivity, anaphylaxis, immunoassay, monitoring cytokine production, monitoring expression of cell adhesion molecules and the like.

For example, to assess the effect of the instant compounds on cytokine production, peripheral blood lymphocytes can be isolated by a known method, washed and set up in a tissue culture dish using a standard tissue culture medium, such as RPMI. Then, a known inducer of cytokine production, such as lipopolysaccharide, is added to the cells as are varying amounts of a test compound of the instant invention. Following incubation, the amount of one or more cytokines can be assessed by any of a variety of techniques, such as an ELISA, many kits of which are commercially available.

Neutrophil migration and infiltration into tissue spaces and the effect thereon of the compounds of the instant compounds can be tested. For example, immune complexes can be developed at a subcutaneous or intradermal site to draw neutrophils and the effect of the instant compounds on neutrophil migration can be assessed. A protocol is as follows. Mice are injected IV with bovine serum albumin (BSA). Then the mice are injected intradermally with antibody to BSA. For experimental animals, the test substance is administered concurrently intradermally or subcutaneously at the site of antibody deposition. After about four hours, the animal is sacrificed, the skin at the injection site is removed and then treated appropriately, such as assaying for myeloperoxidase, to determine the extent of neutrophil migration to the injection site.

Expression of ELAM, ICAM or VCAM can be assessed by standard immunoassay techniques using known and available antibodies and kits (Bochner et al., J. Exp. Med., 173: 1553–1556, 1991; Silber et al., J. Clin. Invest., 93: 1554–1563, 1994).

The instant invention also provides medicaments and methods for treating, for example, inflammatory responses associated with activated endothelial cells and immune system functions or for protecting against liver injury.

Thus, the instant compounds are useful as anti-inflammatory agents for treating diseases, such as rheumatoid arthritis, scleroderma gout, systemic lupus erythematous, ankylosing spondilitis, Sjogren's syndrome, mixed connective tissue disease (MCTD), Reiter's syndrome, systemic necrotizing vasculitis, hypersensitivity vasculitis, temporal arteritis, sarcoidosis, Kawasaki's disease, Buerger's disease, temporal arteritis, midline granuloma, psoriatic arthritis, inflammatory diseases of the joints, insulin resistant diabetes, Hashimoto's thyroiditis, juvenile autoimmune diabetes, myasthenia gravis, ulcerative colitis, cirrhosis, autoimmune uveitis and the like.

The compounds of the instant invention may be useful for inhibiting cytokine production, such as TNF-41, IL-6, IL-1, IL-11, IL-2, Leukemia inhibitory factor, ciliary neurotrophic factor and the like.

Also included are diseases related to cell adhesion molecule expression, such as allergic diseases, for example, asthma, atopic dermatitis, Crohn's disease, sepsis, endotoxin shock, allograft rejection, bacterium infection, i.e., gram-negative infection, cachexia, polyclonal B-cell abnormalities, cardiac myxoma, AIDS, HIV infection, Castleman's disease, alcoholic liver cirrhosis, psoriasis, malignancies, plasmacytoma, myeloma, lymphoma, leukemia, mesangial proliferative glomerulonephritis, cerebral malaria, adult respiratory distress syndrome and the like.

One skilled in the art can readily determine the maladies for which the medicaments and methods of treatment of the instant invention will be useful. Examples include tumor-cell-mediated vascular damage, rheumatoid arthritis, post-reprefusion myocardial injury (damage by granulocytes) and adult respiratory distress syndrome (macrophages and granulocytes). Examples also are disclosed in Simpson et al., J. Clin. Invest., 81: 624–629, 1988; Vedder et al., J. Clin. Invest., 81: 939–944, 1988; Simon & Ward "Adult Respiratory Distress Syndrome" in Inflammation: Basic Principles and Clinical Correlates (Gallin et al., eds.) Raven Press, New York, 1988, page 815; Kadison & Barton "Vasculitis: Mechanisms of Vessel Damage, Id., page 703; and Harris "Pathogenesis of Rheumatoid Arthritis: A Disorder Associated with Dysfunctional Immunoregulation, Id., page 751.

Toxic liver disease is a widely prevalent health problem. The etiology is diverse and it is unclear whether the dysfunction occurs and is manifest at the level of individual hepatocytes or at the level of the tissue or organ. Inherited disorders and hepatoxins, such as lipopolysaccharide (LPS), are used in models of liver injury. Another hepatitis model relates to the use of ConA to precipitate severe liver injury, as assessed by transaminase release and presence thereof in the medium or circulation. The concanavalin A (ConA)-mediated hepatotoxicity is not a function of the sugar specificity or agglutinating activity thereof (Tiegs et al., J. Clin. Invest., 90:196–203, 1992). Moreover, excessive lymphocyte infiltration in the liver is not required for hepatotoxicity (Gantner et al., Hepatol., 21:190–198, 1995).

Early exposure of hosts to compounds of the instant invention affords protection from progressive liver damage, as assessed by a decrease in serum transaminase. Thus, hosts exposed concurrently to a compound of interest and ConA demonstrated enhanced liver function as compared to controls receiving ConA alone. Thus, the instant compounds are useful to protect, or to reduce against liver injury. The thus-obtained active ingredient compounds are effective as immunosuppressants or antiphlogistics and as hepatoprotectants and are used in the form of conventional pharmaceutical preparations. Such preparations are prepared using the conventional fillers, extenders, binding agents, moistening agents, disintegrating agents, surfactants, lubricants and the like diluents or excipients.

The pharmaceutical preparations may have various dosage forms selected according to the purpose of therapy and typical examples thereof are tablets, pills, powders, solutions, suspensions, emulsions, topical preparation, granules, capsules, suppositories, and injections (solutions, suspensions etc.).

For the manufacture of tablets, a wide variety of pharmaceutically acceptable carriers so far well known in the field can be used. Thus, for example, vehicles or excipients, such as lactose, sucrose, sodium chloride, glucose, urea, starch, calcium carbonate, kaolin, crystalline cellulose and silicic acid; binding agents, such as water, ethanol, propanol, simple syrup, glucose solution, starch solution, gelatin solution, carboxymethylcellulose, shellac, methylcellulose, potassium phosphate and polyvinylpyrrolidone; disintegrating agents, such as dry starch, sodium alginate, powdered agar, powdered laminarin, sodium hydrogen carbonate, calcium carbonate, polyoxyethylene sorbitan fatty acid esters, sodium lauryl sulfate and stearic acid monoglyceride, starch and lactose; disintegration inhibitors, such as sucrose, stearin, cacao butter and hydrogenated oils; absorption promoters, such as quaternary ammonium bases and sodium lauryl sulfate; wetting agents or humectants, such as glycerol and starch; adsorbents, such as starch, lactose, kaolin, bentonite and colloidal silica; and lubricants, such as refined talc, stearic acid salts, powdered boric acid and polyethylene glycol can be used.

When necessary, the tablets may be provided further with a conventional coating to give, for example, sugar-coated tablets, gelatin-coated tablets, enteric-coated tablets, film-coated tablets or, double-coated or multilayer tablets.

For the manufacture of pills, a wide variety of carriers well known in the art can be used. Examples include vehicles or excipients, such as glucose, lactose, starch, cacao butter, hardened vegetable oils, kaolin and talc; binding agents, such as powdered gum arabic, powdered tragacanth gum, gelatin and ethanol; and disintegrating agents, such as laminaran and agar.

For the manufacture of suppositories, a wide variety of carriers so far known can be used. Examples of the carrier include polyethylene glycol, cacao butter, higher alcohols, higher alcohol esters, gelatin and semisynthetic glycerides.

Capsules are manufactured, in the conventional manner, usually by filling each active ingredient compound in admixture with various carriers mentioned above into hard gelatin capsules, soft capsules etc. In preparing injections, the solutions, emulsions or suspensions preferably are sterilized and isotonic with blood.

For preparing such dosage forms, any diluent usually used in the field can be employed, such as water, ethyl alcohol, macrogol, propylene glycol, ethoxylated isostearyl alcohol, polyoxylated isostearyl alcohol and polyoxyethylene sorbitan fatty acid esters. The pharmaceutical preparations may contain sodium chloride, glucose or glycerol in an amount sufficient to give isotonic solutions. Conventional solubilizing agents, buffers, soothing agents, local anesthetics or the like may be added. Furthermore, when necessary, the pharmaceutical preparations may contain coloring matter, preservatives, perfumes, flavoring agents, sweetening agents and the like as well as other drugs.

The proportion of the active ingredient compound in the pharmaceutical preparations of the instant invention is not critical but may be selected suitably over a wide range. Generally, however, the proportion is selected within the range of about 1 to about 70% by weight, preferably about 5 to about 50% by weight.

The route of administration of the pharmaceutical preparations of the instant invention is not critical but is selected according to the dosage form, the age of the patient, sex and other factors and the severity of the disease to be treated. Thus, for instance, when provided in the form of tablets, pills, solutions, suspensions, emulsions, granules or capsules, the preparations are administered orally. Injectable solutions are administered intravenously, either alone or in admixture with conventional fluids for parenteral infusion containing glucose, amino acids and so on. When necessary, the solutions also may be administered by the intramuscular, intradermal, subcutaneous or intraperitoneal route. Examples for a liquid preparation include isotonic saline (0.15M NaCl) and Ringer's glucose intravenous solution. The actual dosage can be ascertained empirically based on in vitro, animal or clinical studies using known methods. Suppositories are administered rectally.

The dosage of the pharmaceutical preparations of the invention may be selected appropriately depending on the method of administration, the age of the patient, sex and other factors, severity of the disease and other factors. Generally, however, the daily dose of each active ingredient compound may be within the range of about 0.6 to 50 mg per kilogram of body weight. It is desirable that the active ingredient compound be contained in an amount of about 10 to 1,000 mg in each unit dosage form.

The artisan can configure the appropriate formulation comprising the instant oxadiazoles and seeking guidance from numerous authorities and references, such as "Goodman & Gilman's Pharmaceutical Basis of Therapeutics" (6th ed., Goodman et al., eds., MacMillan Publ. Co., New York, 1980).

In body sites that are characterized by continual cell growth or require cell growth inhibition because of dysfunction and are relatively inaccessible, the instant oxadiazoles can be administered in a suitable fashion to assure effective local concentrations. For example, the instant compounds may be injected in a depot or adjuvant, carried in a surgically situated implant or reservoir that slowly releases a fixed amount of an oxadiazole of the instant invention over a period of time or may be complexed to recognition molecules with the capability of binding to the site presenting with abnormal cell growth. An example of such a contemplated scenario is a recognition molecule that is an antibody with binding specificity for a bone marrow specific antigen wherein said marrow specific antibody is complexed to an oxadiazole, said complex administered to a patient with an immune system malfunction.

The notion of targeting carriers of pharmaceuticals to specific body sites or using carriers to transport pharmaceuticals contained therein is known in the art (Weinstein in "Liposomes: From Biophysics to Therapeutics", Ostrow, ed., Dekker, New York 1987; Heath et al., Proc. Natl. Acad. Sci. 80: 1377–1381, 1983). Examples of carriers are microcapsules, microgranules and liposomes. Specificity of targeting for pharmaceutic delivery is obtained by having binding molecules on the surface of the carrier wherein the binding molecules have an affinity for a complementary molecule expressed on or about the target cell, tissue or organ. Examples of binding molecules are antibodies, hormones and adhesion molecule ligands, with the complementary molecules being antigens, receptors and adhesion molecules. The carriers are fashioned to contain within other binding molecules, immunosuppressants, such as steroids, antibiotics, cytotoxins and the like.

Liposomes are versatile by virtue of having the capabilities of local release, as do some other carriers; of membrane fusion with a target cell resulting in, for example, pericellular or intracellular delivery and cell surface expression of the binding molecules; and of being engulfed by a target cell by endocytosis.

The use of adhesion molecules and adhesion molecule ligands as binding molecules has a particular advantage because those molecules and ligands are "self" and would not normally elicit an immune response. Thus ELAM ligand, VCAM ligand and ICAM ligand are particularly suitable binding molecules for targeting carriers to sites of inflammation because the respective complementary adhesion molecules, ELAM, VCAM and ICAM, respectively, are expressed on activated endothelial cells.

The invention now will be exemplified in the following non-limiting examples.

EXAMPLE 1

Propionic acid hyrazide (11)

To a solution of ethyl propionate (14.9 ml, 0.130 mol) in EtOH (250 ml) was added anhydrous hydrazine (4.90 ml, 0.156 mol) and the mixture was refluxed for 24 h. The reaction was cooled to room temperature and the excess solvent was removed in vacuo to give an oil which crystallizes on standing. The crude solid was rinsed with 1/1 $Et_2O$/hexanes (3×10 ml) to remove remaining hydrazine to give >95% pure propionic acid hydrazide (11) (5.48 g, 47%) as a white solid, 25°–26° C.

EXAMPLE 2

4-Methoxybenzoic acid hydrazide (12)

To a solution of $NH_2NH_2$ (3.9 ml, 0.125 mol) in $CH_2Cl_2$ 250 ml) cooled to 0° C. was added dropwise a solution of 4-methoxybenzoyl chloride (10.6 g, 0.062 mol) in $CH_2Cl_2$ (50 ml). The resulting slurry was stirred in an ice bath for 30 min. and at room temperature for an additional 2 h. The $CH_2Cl_2$ was removed in vacuo and the solid suspended in EtOH (150 ml).

Solid $K_2CO_3$ (5 g) was added and the mixture was stirred for 10 min. The undissolved solids were filtered off and the filtrate recondensed in vacuo to give a yellow solid. Recrystallization from EtOH/$Et_2O$ yielded 4-methoxybenzoic acid hydrazide (12) (7.0 g, 68%) as a white solid, 125°–126° C.

EXAMPLE 3

1-Benzyl-4-chloromethyl-5-methylimidazole hydrochloride (13)

To a solution of 1-benzyl-4-hydroxymethyl-5-methylimidazole (0.85 g, 0.0042 mol), prepared according to the method of Ueda et al., BioMed. Chem. Lett., 4:1623, 1994, in $CHCl_3$ (20 ml) at 0° C. was added $SOCl_2$ (0.421 ml, 0.0126 mol). The reaction was refluxed for 3 h, cooled to rt and the solvent removed in vacuo. The resulting solid was rinsed with $Et_2O$ (3×10 ml) and dried under vacuum to give 1-benzyl-4-chloromethyl-5-methylimidazole hydrochloride (13) as a white solid; mp 188° C.

EXAMPLE 4

2-chloromethyl-5-dimethyl-4-methoxypyridine hydrochloride (14)

To a solution of 3,5-lutidine (42.86, 0.400 mol) in toluene (240 ml) in a three-neck flask, under $N_2$ atmosphere, was added dropwise MeLi [0.33M in ether, 1330 ml (0.44 mol), prepared from CH$_3$I and Li or obtained from Aldrich]. The reaction was stirred and heated at 60°–80° C. for 6 h, after which time the ether was distilled off. The remaining solution was poured into water/crushed ice (200 ml), acidified with conc. HCl and extracted with ethyl acetate (2×100 ml). The aqueous solution then was basified with aq. NaOH and extracted with CH$_2$Cl$_2$ (3×100 ml). The CH$_2$Cl$_2$ extracts were combined, washed with sat. NaCl solution (1×50 ml), dried (MgSO$_4$) and the solvent removed in vacuo. The residue was distilled under reduced pressure to give 2,3,5-trimethylpyridine (35.24 g, 72%) as a pale oil; bp 65°–71° C./11 mmHg. A solution of 2,3,5-trimethylpyridine (36.35 g, 0.30 mol) in AcOH (120 ml) was treated with 30% H$_2$O$_2$ (45 ml) and the mixture heated at 100° C. for 3 h. An additional aliquot of 30% H$_2$O$_2$ (15 ml) was added and the mixture was heated for an additional 10 h at 100° C. The reaction was cooled to rt, diluted with water (100 ml) and concentrated in vacuo. The residue again was diluted with water (200 ml), neutralized with KOH pellets and extracted with CH$_2$Cl$_2$ (3×100 ml). The extracts were combined, washed with sat. NaCl (1×50 ml), dried (MgSO$_4$) and the solvent removed in vacuo to give 2,3,5-trimethylpyridine-N-oxide as a pale yellow solid, (50 g, quant.); mp 41°–42° C. (hexanes, colorless needles).

To a cooled solution of fuming HNO$_3$ (50 ml) and conc. H$_2$SO$_4$ (50 ml) in an ice bath was added 2,3,5-trimethylpyridine-N-oxide (35.67 g) and the reaction mixture was stirred at 40°–50° C. for 18 h. After which time, the reaction was cooled to rt, poured into water/crushed ice (250 ml), alkalized with NaOH pellets and extracted with CH$_2$Cl$_2$ (3×100 ml). The extracts were combined and washed with sat. NaCl (1×50 ml), dried (MgSO$_4$) and the solvent removed in vacuo to give 4-nitro-2,3,5-trimethyl-pyridine-N-oxide (45.5 g, 96%) as an orange solid; mp 69°–71° C. (ether), orange plates.

To a solution of sodium methoxide, prepared from Na (8.62 g, 0.375 mol) and MeOH (500 ml), was added 4-nitro-2,3,5-trimethylpyridine-N-oxide (45.5 g, 0.25 mol). The reaction mixture was refluxed for 5 h, cooled to rt and most of the solvent removed in vacuo. The slurry was diluted with water (100 ml) and extracted with CH$_2$Cl$_2$ (3×100 ml). The extracts were combined, washed with sat. NaCl solution, dried (MgSO$_4$) and the solvent removed in vacuo to give 4-methoxy-2,3,5-trimethylpyridine-N-oxide as a semi-solid (37.5 g, 90%).

A solution of 4-methoxy-2,3,5-trimethylpyridine-N-oxide (23 g) in Ac$_2$O (150 ml) was stirred at 100° C. for 1.5 h. Acetic anhydride was removed in vacuo and the slurry was diluted with 15% aq. HCl and heated at 50°–55° C. for 3 h. The remaining acetylated product was hydrolyzed by the addition of conc. HCl (15 ml) and heating 50°–55° C. for an additional 2 h. The reaction mixture was cooled to rt and neutralized with solid K$_2$CO$_3$ and extracted with CH$_2$Cl$_2$ (3×100 ml). The extracts were combined, washed with dried (MgSO$_4$) and the solvent removed in vacuo to give crude 2-hydroxymethyl-3,5-dimethyl-4-methoxypyridine (25 g, crude).

To a solution of crude 2-hydroxymethyl-3,5-dimethyl-4-methoxypyridine (23.41 g, 0.41 mol) in CHCl$_3$ (70 ml) was added SO$_2$Cl$_2$ (30 ml, 0.42 mol) at ice bath temperature. The reaction mixture was refluxed for 2 h and cooled to rt. Evaporation of the solvent in vacuo gave a dark brown solid. Recrystallization from isopropanol-ether gave 2-chloromethyl-3,5-dimethyl-4-methoxypyridine hydrochloride (14) (21.6 g, 69%) as a white solid; mp 135°–136° C. For previous syntheses see references cited in Brandstrom et al., Acta Chemica Scandinavia 43: 536–548, 1989 and GB 2134523.

EXAMPLE 5

9-Choloro-4-methoxy-6,7,8,9-tetrahydro-5H-cyclohepta[b]pyridine hydrochloride (15)

2,3-Cycloheptenopyridine (5.0 g, 0.034 mol) was dissolved in AcOH (15 ml) and treated with 30% H$_2$O$_2$ (7 ml). The reaction mixture was heated to 100° C. for 20 h. The reaction mixture was cooled to rt, diluted with water (25 ml) and most of the solvent removed in vacuo. An additional portion of water was added (25 ml) and the mixture made basic using KOH pellets and then extracted with CH$_2$Cl$_2$ (4×30 ml). The extracts were combined, washed with sat. NaCl solution, dried (MgSO$_4$) and the solvent removed in vacuo to give 2,3-cycloheptenopyridine-N-oxide (5.4 g, quant.) as a solid; mp 106°–107° C.

To fuming HNO$_3$ (25 ml) was added 2,3-cycloheptenopyridine-N-oxide (5.4 g, 0.033 mol) and the mixture refluxed for 45 h. The reaction mixture was cooled to rt, alkalized using NaOH pellets and extracted with CH$_2$Cl$_2$ (4×30 ml). The extracts were combined, washed with sat. NaCl solution, dried (MgSO$_4$) and solvent removed in vacuo to give 4-nitro-2,3-cycloheptenopyridine-N-oxide (4.2 g, 66%) as a solid; mp 116° C.

To a solution of sodium methoxide under a N$_2$ atmosphere, prepared from Na (1.02 g, 0.040 mol) and MeOH (50 ml), was added 4-nitro-2,3-cycloheptenopyridine-N-oxide (4.5 g, 0.020 mol). The reaction mixture was refluxed for 5 h, cooled to rt and most of the solvent removed in vacuo. The resulting slurry was diluted with water (50 ml) and extracted with CH$_2$Cl$_2$ (3×40 ml). The extracts were combined, washed with sat. NaCl (1×25 ml), dried (MgSO$_4$) and the solvent removed in vacuo to give 4-methoxy-2,3-cycloheptenopyridine-N-oxide (3.0 g, 77%) as a solid; mp 132°–134° C.

A solution of 4-methoxy-2,3-cycloheptenopyridine-N-oxide (2.85 g, 0.015 mol) in Ac$_2$O (25 ml) was heated at 100° C. for 2 h. The reaction mixture was cooled to rt and most of the Ac$_2$O removed in vacuo. The remaining material was diluted with 15% HCl (30 ml) and heated at 65° C. After heating 3 h, conc. HCl (2 ml) was added. The reaction stirred further at 65° C. for 2 h, cooled to rt, made basic with solid K$_2$CO$_3$ and extracted with CH$_2$Cl$_2$ (4×25 ml). The extracts were combined, washed with sat. NaCl (1×25 ml), dried (MgSO$_4$) and the solvent removed in vacuo to give crude 9-hydroxy-4-methoxy-6,7,8,9-tertrahydro-5H-cyclohepta[b]pyridine. Chromatography on silica gel using ethyl acetate/hexanes (1/1) gave pure 9-hydroxy-4-methoxy-6,7,8,9-tertrahydro-5H-cyclohepta[b]pyridine as a solid (1.31 g, 45%); mp 117°–118° C. 9-Hydroxy-4-methoxy-6,7,8,9-tertahydro-5H-cyclohepta[b]pyridine (1.31, 0.0063 mol) was dissolved in CHCl$_3$ (10 ml) and treated with SO$_2$Cl$_2$ (0.736 ml, 9.4 mol). The reaction mixture was refluxed for 4 h, cooled to rt and the solvent removed in vacuo to give a solid. The solid was rinsed with ether (2×10 ml) and dried under vacuum to give 9-chloro-4-methoxy-6,7,8,9-tertrahydro-5H-cyclohepta[b]pyridine hydrochloride (15) solid (1.6 g, quant.); mp 144°–146° C. See Yamada et al., Chem. Pharm. Bull. 42: 718, 1994.

EXAMPLE 6

2-(3,5-dimethyl-4-methoxy-2-pyridyl) methylsulfinyl-5-methyl-1,3,4-oxadiazole (70)

Acetic acid hydrazide (Aldrich) (101 g, 1.36 mol) was dissolved in EtOH (1000 ml) and treated sequentially with CS$_2$ (210 ml, 3.49 mol) and powdered KOH (76.5 g, 1.36 mol). The mixture then was refluxed for 25 h. After cooling to room temperature, the solids were filtered and filtrate condensed in vacuo to give the potassium salt of 2-mercapto-5-methyl-1,3,4-oxadiazole.

$CH_2Cl_2$ was added to the residue and the insoluble materials were filtered off. The $CH_2Cl_2$ solution was evaporated in vacuo to give an oil which was purified by silica gel chromatography using $CH_2Cl_2$/MeOH (10/1) as the eluant. Recrystallization from ethyl acetate/hexanes gave 2-mercapto-5-methyl-1,3,4-oxadiazole (120 g, 76%) as a white solid, 76°–77° C.; literature mp. 78° C., Hoggarth, J. Chem. Soc., 4811, 1952.

To a solution of 2-mercapto-5-methyl-1,3,4-oxadiazole (10.5 g, 0.090 mol) in acetone (250 ml) were added $K_2CO_3$ (44.8 g, 0.324 mol) and 2-chloromethyl-3,5-dimethyl-4-methoxypyridine hydrochloride (18.0 g, 0.081 mol). The mixture was refluxed for 8 h. After cooling to room temperature, water (250 ml) and $CH_2Cl_2$ (200 ml) were added and the organic layer collected. The aqueous layer was extracted with $CH_2Cl_2$ (3×50 ml).

The organic extracts were combined and washed with water (1×50 ml), brine (1×50 ml), dried ($Na_2SO_4$) and the solvent removed in vacuo. The residue was purified on silica gel chromatography using $CH_2Cl_2$/MeOH (10/1) to give 2-(3,5-dimethyl-4-methoxy-2-pyridyl)methylthio-5-methyl-1,3,4-oxadiazole (16) (1.6 g, 86%) as a solid; mp 87°–89° C.

To an ice bath-cooled solution of 2-(3,5-dimethyl-4-methoxy-2-pyridyl)methylthio-5-methyl-1,3,4-oxadiazole (26.8 g, 0.100 mol) in dry $CH_2Cl_2$ (300 ml) was added in portions m-chloroperoxybenzoic acid (m-CPBA) (25 g, 0.120 mol, 80%). Stirring was maintained for total of 2 h and then the mixture was treated with sat. aq. $Na_2S_2O_3$ (25 ml) and saturated aq. $Na_2CO_3$ (10 ml).

The organic layer was separated and the aqueous layer was extracted with $CH_2Cl_2$ (3×50 ml), dried ($Mg_2SO_4$) and the solvent evaporated in vacuo. The residue was purified by silica gel chromatography using ethyl acetate to $CH_2Cl_2$/MeOH (20/1) to give 2-(3,5-dimethyl-4-methoxy-2-pyridyl)methylsulfinyl-5-methyl-1,3,4-oxadiazole (70) (5.44 g, 19%, mp 114°–115° C.) along with unreacted starting material (3.82 g) and the N-oxidized products 2-(5-methyl-1,3,4-oxadiazol-2-yl)thiomethyl-3,5-dimethyl-4-methoxypyridine-N-oxide and 2-(5-methyl-1,3,4-oxadiazol-2-yl)sulfinylmethyl-3,5-dimethyl-4-methoxypyridine-N-oxide (15.76 g).

EXAMPLE 7

2-(2,6-dimethylphenyl)sulfinyl-5-methyl-1,3,4-oxadiazole (78)

To an NaH slurry (0.15 g, 0.0037 mol, 60% in oil) in dry DMF (5 ml) under a $N_2$ atmosphere was added 2,6-dimethylthiophenol (0.50 ml, 0.00374 mol). The mixture was stirred for 10 min at rt and cooled to 0° C. To the cooled solution was added dropwise via syringe a solution of 5-methyl-2-sulfinylmethyl-1,3,4-oxadiazole (77) (0.5 g, 0.0034 mol) in dry DMF (1.5 ml). The mixture was stirred for 1 h, water was added (15 ml) and the aqueous layer extracted with $Et_2O$ (4×20 ml). The combined extracts were washed with water (2×25 ml), saturated NaCl solution (1×25 ml), dried ($MgSO_4$) and solvent removed in vacuo. Chromatography on silica gel using ½ ethyl acetate/hexanes gave 2-(2,6-dimethylphenyl)thio-5-methyl-1,3,4-oxadiazole (24) as a white solid (0.372 g, 46%, mp 53°–54° C.).

To an ice-cooled solution of 2-(2,6-dimethylphenyl)thio-5-methyl-1,3,4-oxadiazole (0.350 g, 0.0016 mol) in $CH_2Cl_2$ (10 ml) was added dropwise m-CPBA (0.530 g, 0.002 mol, 65% pure) in $CH_2Cl_2$ (5 ml). The ice bath was removed and the reaction mixture was stirred at rt for 2 h and treated with sat. aq. $Na_2S_2O_3$ (2.5 ml) solution and sat. aq. $Na_2CO_3$ (10 ml). The organic layer was separated and then the aqueous layer was extracted with $CH_2Cl_2$ (2×25 ml), dried ($MgSO_4$) and the solvent evaporated in vacuo. Chromatography on silica gel using ethyl acetate/hexanes (1/1) as the eluant gave 2-(2,6-dimethylphenyl)sulfinyl-5-methyl-1,3,4-oxadiazole (78) (0.125 g, 23%) as a white solid; mp 79°–80° C.

EXAMPLE 8

2-(2,6-ditertbutyl-4-hyroxyphenyl)sulfinyl-5-(2-pyridyl)-1,3,4-oxadiazole (98)

To a solution of 2-pyridyl acid hydrazide (13.7 g, 0.100 mol) in EtOH (200 ml) was added $CS_2$ (15.0 ml, 0.250 mol) followed by the addition of powdered KOH (6.6 g, 0.100 mol, 85% pure) in portions. The mixture was refluxed for 24 h, cooled to rt and the solvent removed in vacuo to give a solid.

The solid was rinsed with 1:1 EtOH/$Et_2O$ (150 ml) and the residual solvent is removed under reduced pressure to give >90% potassium salt of 5-(2-pyridyl)-1,3,4-oxadiazole-2-thiol (21 g, crude) as judged by 1H NMR.

To a stirring heterogeneous mixture of 5-(2-pyridyl)-1,3,4-oxadiazole-2-thiol potassium salt (2.17 g, 0.19 mol) in DMF (25 ml) under an $N_2$ atmosphere, was added 2.85 g (0.01 mol) of 4-bromo-2,6-ditertbutylphenol. The mixture was stirred for 24 h at 110° C. After cooling, the slurry was diluted with water (100 ml) and extracted with $Et_2O$ (4×35 ml). The $Et_2O$ extracts were combined and washed with water (2×50 ml) and saturated NaCl solution (50 ml) and then dried ($MgSO_4$). The solvent was removed in vacuo to give a solid. Chromatography on silica gel using 1/4 ethyl acetate/hexanes gave 2-(2,6-ditertbutyl-4-hydroxyphenyl)thio-5-(2-pyridyl)-1,3,4-oxadiazole (45) as a white solid (1.5 g, 40% yield; mp 128°–129° C.).

To a solution of 2-(2,6-ditertbutyl-4-hydroxyphenyl)thio-5-(2-pyridyl)-1,3,4-oxadiazole (1.25 g, 0.00325 mol) in $CH_2Cl_2$ (30 ml) at rt was added dropwise a solution of mCPBA (1.04 g, 0.0039 mol, 65% pure) in $CH_2Cl_2$ (25 ml) over 30 min. The reaction was stirred at rt for an additional 1.5 h and treated with sat aq. $Na_2S_2O_3$ (5 ml) and sat. aq. $Na_2CO_3$ (20 ml). The organic layer was separated and the aqueous layer was extracted with $CH_2Cl_2$ (3×25 ml), dried ($MgSO_4$) and the solvent evaporated in vacuo. Chromatography on silica gel using ethyl acetate/hexanes (1/1) as the eluant gave 2-(2,6-di-tertbutyl-4-hydroxyphenyl)sulfinyl-5-(2-pyridyl)-1,3,4-oxadiazole (98) as a white solid (0.900 g, 70%); m.p. 172.5°–173.0° C.

EXAMPLE 9

By methods similar to those set forth in the examples and teachings hereinabove using available starting materials, the following compounds of interest were synthesized.

TABLE 1

$$\underset{R_1}{\overset{N-N}{\diagdown}}\underset{O}{\diagup}\overset{}{\diagdown}\underset{S}{\diagup}R_2$$

| Compound | R₁ | R₂ | Yield (%) | M.P. (°C.) or ¹H NMR |
|---|---|---|---|---|
| 16 | CH₃ | (A) 4-methoxy-3,5-dimethylpyridin-2-ylmethyl | 86 | 87.0 |
| 17 | CH₃ | (B) pyridin-2-ylmethyl | 63 | 31.5 |
| 18 | CH₃ | (C) benzyl | 65 | oil, ¹H(CDCl₃) 7.44–7.31(2H, m), 7.30–7.12(3H, m), 4.44(2H, s), 2.48(3H, s) |
| 19 | CH₃ | 4-methoxy-6,7,8,9-tetrahydro-5H-cyclohepta[b]pyridin-9-ylmethyl | 92 | 80.0 |
| 20 | CH₃ | 3-(4-tert-butylphenyl)-1,2,4-oxadiazol-5-ylmethyl | 64 | 58.0 |
| 21 | CH₃ | (1-benzyl-1H-imidazol-2-yl)methyl | 54 | oil, ¹H(CDCl₃) 7.40—7.26(3H, m) 7.15–7.00(2H, m), 7.03(1H, d, J=1.2Hz) 6.88(1H, d, J=1.2Hz), 5.27(2H, s), 4.51 (2H, s), 2.48(3H, s) |
| 22 | CH₃ | (1-benzyl-4-methyl-1H-imidazol-5-yl)methyl | 97 | oil, ¹H(CDCl₃) 7.44(1H, s), 7.41 (3H, m), 7.05(2H, d, J=7.8Hz), 5.02 (2H, s), 4.43(2H, s), 2.48(3H, s), 2.13(3H, s) |
| 23 | CH₃ | CH₃ | 92 | 63.0 |
| 24 | CH₃ | 2,6-dimethylphenyl | 46 | 53.0 |
| 25 | CH₃CH₂ | A | 69 | 76.0 |
| 26 | CH₃(CH₂)₂ | A | 90 | 52.5 |
| 27 | CH₃(CH₂)₃ | A | 90 | 60.0 |
| 28 | CH₃(CH₂)₄ | A | 90 | 44.0 |
| 29 | CH₃(CH₂)₆ | A | 91 | 44.0 |
| 30 | CH₃(CH₂)₈ | A | 99 | 54.0 |

TABLE 1-continued
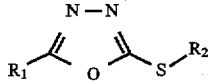
| Compound | R₁ | R₂ | Yield (%) | M.P. (°C.) or ¹H NMR |
|---|---|---|---|---|
| 31 | 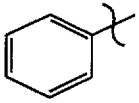 | A | 90 | 155.0 |
| 32 | 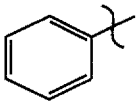 | C | 95 | 93.5 |
| 33 | 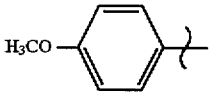 | B | 59 | 97.5 |
| 34 | 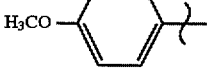 | C | 57 | 79.0 |
| 35 |  | A | 85 | 154.0 |
| 36 |  | B | 95 | 111.0 |
| 37 |  | C | 95 | 97.0 |
| 38 | 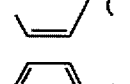 | A | 48 | 142.0 |
| 39 | 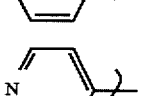 | B | 82 | 132.5 |
| 40 | 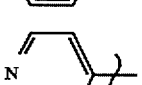 | C | 55 | 106.0 |
| 41 |  | 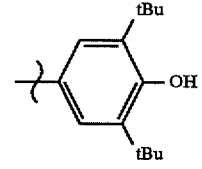 | 12 | 184.0 |
| 42 | 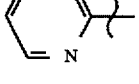 | A | 51 | 112.0 |

TABLE 1-continued
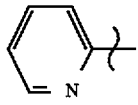
| Compound | R₁ | R₂ | Yield (%) | M.P. (°C.) or ¹H NMR |
|---|---|---|---|---|
| 43 | 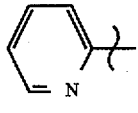 | B | 75 | 102.0 |
| 44 | 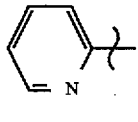 | C | 94 | 91.5 |
| 45 | 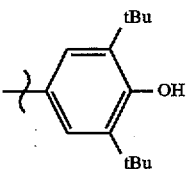 | 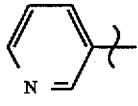 | 39 | 128.0 |
| 46 | 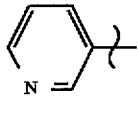 | A | 47 | 134.0 |
| 47 | 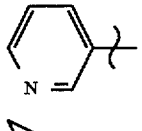 | B | 72 | 103.0 |
| 48 | 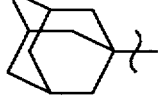 | C | 97 | 72.5 |
| 49 | 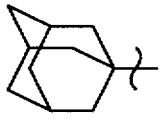 | B | 66 | 83.0 |
| 50 | 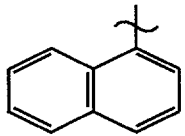 | C | 71 | oil, ¹H(CDCl₃) 7.50–7.38(2H, m), 7.38–7.25(3H, m), 4.43(2H, s), 2.09 (3H, s), 2.02(5H, bs), 1.88–1.74(6H, m) 1.63(1H, s) |
| 51 | 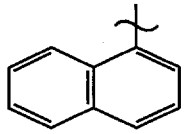 | B | 57 | 76.0 |
| 52 | 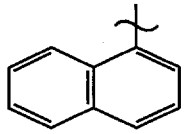 | C | 52 | 58.0 |
| 53 | 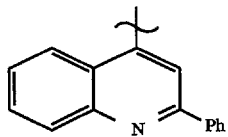 | C | 86 | 138.0 |

TABLE 1-continued
$$R_1 \underset{O}{\overset{N-N}{\nwarrow}} \underset{S}{\overset{}{\diagup}} R_2$$
| Compound | R₁ | R₂ | Yield (%) | M.P. (°C.) or ¹H NMR |
|---|---|---|---|---|
| 54 | 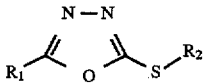 | C | 41 | 112.0 |
| 55 |  | C | 96 | 111.0 |
| 56 | 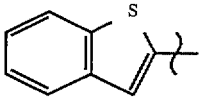 | C | 98 | 156.5 |
| 57 |  | C | 99 | 98.0 |
| 58 | 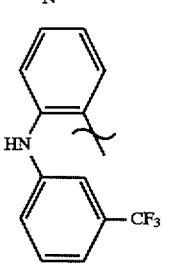 | C | 98 | 124.0 |
| 59 | 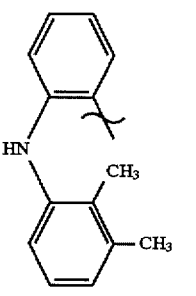 | A | 96 | 130.0 |
| 60 | 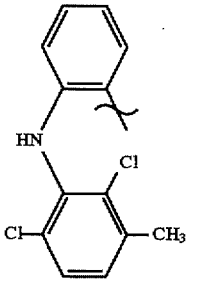 | A | 77 | 153.5 |
| 61 | 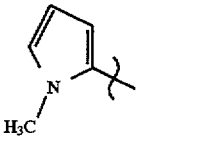 | C | 96 | 86.0–88.0 |

TABLE 1-continued $$R_1 \underset{O}{\overset{N-N}{\diagup}} \underset{S}{\diagdown} R_2$$

| Compound | R₁ | R₂ | Yield (%) | M.P. (°C.) or ¹H NMR |
|---|---|---|---|---|
| 62 | 2-hydroxyphenyl | 9-(4-methoxy-6,7,8,9-tetrahydro-5H-cyclohepta[b]pyridinyl) | 46 | Oil, ¹H(CDCl₃) 8.26(1H, d, J=6.0Hz), 7.73 (1H, d, J=6.0Hz), 7.43(1H, t, J=1.2Hz), 7.11 (1H, d, J=6.0Hz), 7.02(1H, t, J=1.2Hz), 5.45 (1H, m), 3.88(3H, s), 3.45(1H, m), 2.50(2H, m) 2.00(4H, m), 1.50(1H, m) |
| 63 | 3-(trifluoromethyl)phenyl | A | 80 | 145.0 |
| 64 | 4-(trifluoromethyl)phenyl | A | 51 | 167.0 |
| 65 | 3-fluorophenyl | A | 51 | 133.0 |
| 66 | 4-fluorophenyl | A | 59 | 160.0 |
| 67 | 4-phenyl-2-thiazolyl | A | 90 | Decomp. @ 110° C. |
| 68 | 4-phenyl-2-thiazolyl | C | 86 | 98.0 |
| 69 | 4-phenyl-2-thiazolyl | 9-(4-methoxy-6,7,8,9-tetrahydro-5H-cyclohepta[b]pyridinyl) | 80 | 75.0–76.5 |
| 70 | CH₃ | (A) 4-methoxy-3,5-dimethyl-2-pyridinyl | 19 | 114.0 |

TABLE 1-continued $$\underset{R_1}{\overset{N-N}{\underset{O}{\parallel}}}\overset{R_2}{\underset{S}{\parallel}}$$

| Compound | R₁ | R₂ | Yield (%) | M.P. (°C.) or ¹H NMR |
|---|---|---|---|---|
| 71 | CH₃ | (B) 2-pyridylmethyl | 15 | 67.0 |
| 72 | CH₃ | (C) benzyl | 90 | 48.0 |
| 73 | CH₃ | 4-methoxy-6,7,8,9-tetrahydro-5H-cyclohepta[b]pyridin-9-yl | 58 | 99.0 |
| 74 | CH₃ | 3-(4-tert-butylphenyl)-1,2,4-oxadiazol-5-ylmethyl | 82 | 101.0 |
| 75 | CH₃ | 1-benzyl-imidazol-2-ylmethyl | 41 | 99.0 |
| 76 | CH₃ | 1-benzyl-imidazol-4-ylmethyl | 51 | 82.5 |
| 77 | CH₃ | CH₃ | 50 | oil; ¹H(CDCl₃) 3.21(3H, s), 2.67(3H, s) |
| 78 | CH₃ | 2,6-dimethylphenyl | 23 | 79.0 |
| 79 | CH₃CH₂ | A | 33 | 50.0 |
| 80 | CH₃(CH₂)₂ | A | 43 | 29.0 |
| 81 | CH₃(CH₂)₃ | A | 16 | oil; ¹H(CDCl₃) 8.12(1H, S), 4.84(2H, t (dd), J₁=J₂13.8Hz), 3.78(3H, S), 2.96 (2H, t, J=7.6Hz), 2.32(3H, S), 2.24(3H, S), 1.83(2H, m), 1.47((2H, m), 0.98(3H, t, J=7.2Hz,) |
| 82 | CH₃(CH₂)₄ | A | 15 | oil; ¹H(CDCl₃) 8.10(1H, S), 4.83(2H, dd, J₁=J₂=13.8Hz), 3.76(3H, S), 2.94(2H, t, J=7.6Hz), 2.31(3H, S), 2.23(3H, S), 1.83(2H, m), 1.40(4H, m), 0.92(3H, t, J=7.2Hz,) |
| 83 | CH₃(CH₂)₆ | A | 22 | 34.0 |
| 84 | CH₃(CH₂)₈ | A | 25 | 36.0 |

TABLE 1-continued structure: R₁–C(=O)–O–C(=N–N)–S–R₂ (heterocycle)

| Compound | R₁ | R₂ | Yield (%) | M.P. (°C.) or ¹H NMR |
|---|---|---|---|---|
| 85 | phenyl | A | 24 | 134.0 |
| 86 | phenyl | C | 94 | 84.0 |
| 87 | 4-H₃CO-phenyl | B | 40 | 103.5 |
| 88 | 4-H₃CO-phenyl | C | 90 | 76.5 |
| 89 | 2-thienyl | A | 38 | 129.5 |
| 90 | 2-thienyl | B | 21 | 89.0 |
| 91 | 2-thienyl | C | 50 | 111.0 |
| 92 | 4-pyridyl | B | 15 | 115.0 |
| 93 | 4-pyridyl | C | 25 | 109.0 |
| 94 | 4-pyridyl | 3,5-di-tBu-4-OH-phenyl | 30 | 164.0 |
| 95 | 2-pyridyl | A | 15 | oil; ¹H(CDCl₃) 8.83(1H, d, J=4.8Hz), 8.27(1H, d, J=7.8Hz), 8.10(1H, s), 7.92(1H, t, J=7.8Hz), 7.53(1H, m), 4.95(2H, t, J=13.8), 3.76(3H, s), 2.33(3H, s), 2.21(3H, s) |
| 96 | 2-pyridyl | B | 17 | 118.5 |

TABLE 1-continued
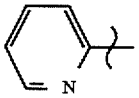
| Compound | R₁ | R₂ | Yield (%) | M.P. (°C.) or ¹H NMR |
|---|---|---|---|---|
| 97 | 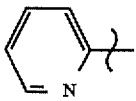 | C | 33 | 105.0 |
| 98 | 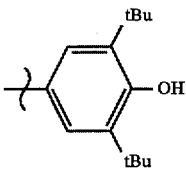 | 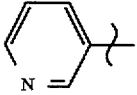 | 70 | 172.5 |
| 99 | 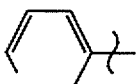 | A | 15 | oil; ¹(CDCl₃) 9.34(1H, s), 8.84(1H, d, J=4.8Hz), 8.42(1H, d, J=9.2Hz), 8.09(1H, s), 7.51(1H, t, J=6.4Hz), 4.93(2H, t, J=13.8Hz), 3.77(3H, s), 2.34(3H, s), 2.22(3H, s) |
| 100 | 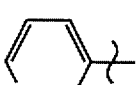 | B | 14 | 103.0 |
| 101 | 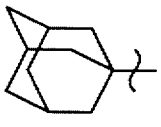 | C | 50 | 96.0 |
| 102 | 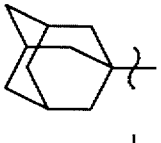 | B | 15 | 96.5 |
| 103 | 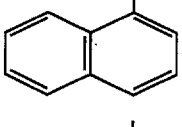 | C | 91 | 65.0 |
| 104 | 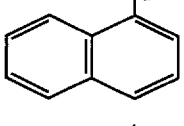 | B | 10 | 83.0 |
| 105 | 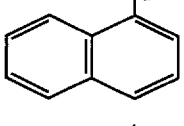 | C | 22 | 142.0 |
| 106 | 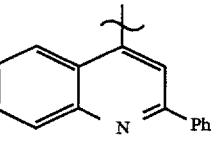 | C | 14 | 186.0 |
| 107 | 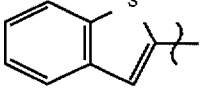 | C | 58 | 161.0 |

TABLE 1-continued $$\underset{R_1}{\overset{N-N}{\underset{O}{\parallel}}}\underset{S}{\overset{}{\parallel}}R_2$$

| Compound | R₁ | R₂ | Yield (%) | M.P. (°C.) or ¹H NMR |
|---|---|---|---|---|
| 108 | 3-substituted 2-phenoxypyridine | C | 22 | 113.0 |
| 109 | 2-(3-trifluoromethylphenylamino)phenyl | C | 63 | 103.0 |
| 110 | 2-(2,3-dimethylphenylamino)phenyl | C | 67 | 112.0 |
| 111 | 2-(2,6-dichloro-3-methylphenylamino)phenyl | C | 18 | 189.0 |
| 112 | 1-methyl-2-pyrrolyl | A | 14 | 146.0 |
| 113 | 2-hydroxyphenyl | A | 19 | 161.0 |
| 114 | 2-hydroxyphenyl | C | 45 | 125.0 |

TABLE 1-continued $$R_1 \underset{O}{\overset{N-N}{\diagup\!\!\!\diagdown}} S^{R_2}$$

| Compound | R₁ | R₂ | Yield (%) | M.P. (°C.) or ¹H NMR |
|---|---|---|---|---|
| 115 | 2-hydroxyphenyl | 4-methoxy-6,7,8,9-tetrahydro-5H-cyclohepta[b]pyridin-9-yl | 42 | Oiil; 1/1 diastereomeric mixture, ¹H(CDCl₃) representative peaks; 5.20(1H, m), 4.80 (1H, m), 3.84(3H, s), 3.82(3H, s) |
| 116 | 3-CF₃-phenyl | A | 80 | 145.0 |
| 117 | 4-CF₃-phenyl | A | 15 | 119.0 |
| 118 | 3-F-phenyl | A | 12 | 116.0 |
| 119 | 4-F-phenyl | A | 13 | 133.0 |
| 120 | 4-phenyl-2-thiazolyl | A | 14 | 82.0 |
| 121 | 4-phenyl-2-thiazolyl | C | 57 | 144.0 |
| 122 | 4-phenyl-2-thiazolyl | 4-methoxy-6,7,8,9-tetrahydro-5H-cyclohepta[b]pyridin-9-yl | 33 | 110.0–113.0 |

EXAMPLE 10

An i.v. injection of 100 µl of BSA at 10 mg/ml in saline was followed by a 25 µl injection of anti-BSA i.d. on the back side of a pre-shaven C57BL/6 mouse. At time 0, along with the BSA and anti-BSA, the test compound or vehicle was administered i.d. at the site of the antibody injection in a volume of 25 µl (for example, 0.5 mg/µl solution). Four hours post injection, the skin was removed and a myeloperoxidase (MPO) assay performed (Mulligan et al., J. Imm. 151(10): 5666–5674, 1993).

Briefly, the skin sample was placed in a 17×100 mm test tube containing 2 ml of ice cold buffer (PBS, pH 7.4). The sample was ground for 30 seconds and placed on ice. The sample was vortexed for 10 seconds and then sonicated for three minutes in iced water. The sample was frozen in dry ice for 30 minutes. The sample then was thawed rapidly in a water bath for 10 minutes. An aliquot of 1.5 ml was removed and placed in a microfuge tube. The sample was spun at high speed in a cold room for 15 minutes. The sample then was titrated across the wells in a microtiter plate with the first well containing a 1:3 dilution of sample, for example, 50 μl of sample and 150 μl of buffer. Substrate and hydrogen peroxide were added to each well. Following a suitable incubation period, sodium azide was added to the wells and the absorbance monitored in a spectrophotometer at 460 nm.

When lung samples are used, 8 μl of sample were added to 192 μl of buffer in the first well and the succeeding samples were diluted serially therefrom.

With compound 68 for example, a decrease in MPO activity of approximately 55–60% was observed.

Similar results with other compounds were obtained as set forth in the Table below.

TABLE 3

| Compound | % Inhibition of of Neutrophil migration (12.5 mg of drug/site) |
|---|---|
| 70 | 55 |
| 71 | 40 |
| 75 | 20 |
| 76 | 20 |
| 85 | 25 |
| 91 | 40 |
| 92 | 60 |
| 93 | 56 |
| 96 | 70 |
| 97 | 80 |
| 100 | 60 |
| 101 | 50 |
| 102 | 25 |
| 113 | 20 |

EXAMPLE 11

The following were used in an ELISA for cell surface molecules: Costar 96-well TC plates, 2% gelatin, 1% BSA-Dulbecco's PBS w/CaMg$^{++}$, IL-1β, primary antibody e.g., 7A9 for ELAM (EP 505749) secondary biotinylated goat anti-mouse IgG/IgM, streptavidin-peroxidase, OPD substrate tablets and 30% hydrogen peroxide.

To begin, 96-well plates were coated with 2% gelatin (1 hour). The excess gelatin was aspirated from the wells. HUVEC's were seeded at 20,000 cells/well in a 200 μl volume.

Prior to assay, the test compounds were dissolved in DMSO at a stock concentration of 3 mg/ml. The stock solutions were set at room temperature and observed to see if dissolution was complete. When monolayers reached confluence (24–28 hours after seeding) the test compounds were added to the wells at final concentrations of 10 μg/ml, 3 μg/ml and 1 μg/ml. The plates were incubated for 1 hour at 37° C. Then, IL-1β at a final concentration of 1 μg/ml was added and the plates incubated for 4 hours at 37° C. The supernatant was removed from the plates by flicking into a sink. The wells were washed 3× with 1% BSA-Dulbecco's PBS.

Primary antibody (7A9 for ELAM or a suitable antibody for VCAM or ICAM) at a concentration of 2.5 μg/ml in a 50 μl volume was added to each well. The plates were incubated at 4° C. for 45 minutes to 1 hour. The wells were washed 3× with 1% BSA Dulbecco's PBS. Secondary antibody (biotinylated goat anti-mouse IgG-IgM, commercially available) at 50 μl/well at a final dilution of 1:1,000 was added to the well and the plates were incubated for 45 minutes to 1 hour at 4° C. The wells were washed 3× with 1% BSA-Dulbecco's PBS.

Streptavidin-peroxidase at 50 μl/well with a final dilution of 1:3,000 was added to each well and the plates were incubated at 4° C. for 30 minutes. Again the plates were washed 3× with 1% BSA-Dulbecco's PBS.

Substrate solution (OPD tablets, citric acid buffer and hydrogen peroxide solution) was prepared and added at 100 μl/well. The plates were incubated 15 minutes at room temperature on a plate shaker and the reaction was stopped with 12.5% sulfuric acid. Plates were read for absorbance values at 492 nm.

The degree of inhibition in expression of ELAM or VCAM by a compound of the instant invention is manifest as a decrease in specific primary antibody binding. In the following table the $IC_{50}$ values are provided using a representative sampling of compounds of the instant invention.

TABLE 4

| | % inhibition @ 3 μg/ml | |
|---|---|---|
| Compound | ELAM | VCAM |
| 70 | 55 | 65 |
| 71 | 30 | 40 |
| 72 | 15 | 25 |
| 73 | 20 @ 10 μg/mL | 20 @ 10 μg/mL |
| 75 | 55 | 100 |
| 79 | 35 | 50 |
| 80 | 45 | 70 |
| 81 | 10 | 20 |
| 85 | 100 | 100 |
| 89 | 25 @ 1 μg/mL | 60 @ 1 μg/mL |
| 91 | 20 @ 1 μg/mL | 20 @ 1 μg/mL |
| 92 | 100 | 100 |
| 93 | 30 @ 1 μg/mL | 25 @ 1 μg/mL |
| 96 | 50 @ 1 μg/mL | 50 @ 1 μg/mL |
| 97 | 50 @ 1 μg/mL | 55 @ 1 μg/mL |
| 100 | 100 | 80 |
| 101 | 75 @ 10 μg/mL | 40 @ 10 μg/mL |
| 102 | 30 | 30 |
| 106 | 10 | 10 |
| 112 | 25 @ 1 μg/mL | 65 @ 1 μg/mL |
| 113 | 30 @ 1 μg/mL | 50 @ 1 μg/mL |
| 114 | 20 @ 1 μg/mL | 25 @ 1 μg/mL |
| 116 | 10 | 25 |
| 117 | 10 | 15 |
| 121 | 40 | 50 |

EXAMPLE 12

| | |
|---|---|
| 2-Benzylthio-5-(2-thienyl)-1,3,4-oxadiazole | 150 g |
| Avicel (trade name, product of Asahi Chemical Industry) | 40 g |
| Corn starch | 30 g |
| Magnesium stearate | 2 g |
| Hydroxypropylmethylcellulose | 10 g |
| Polyethylene glycol 6000 | 3 g |
| Castor oil | 40 g |
| Ethanol | 40 g |

The active ingredient of the invention, Avicel, corn starch and magnesium stearate are combined and ground together and the resulting mixture is tableted. The tablets obtained are coated with a film coating composition composed of hydroxypropylmethyl-cellulose, polyethylene glycol 6000, castor oil and ethanol to give film-coated tablets.

EXAMPLE 13

| | |
|---|---|
| 2-Benzylsulfinyl-5-(4-pyridyl)-1,3,4-oxadiazole | 150 g |
| Citric acid | 1.0 g |
| Lactose | 33.5 g |

-continued

| | |
|---|---|
| Dicalcium phosphate | 70.0 g |
| Pluronic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active ingredient of the invention, citric acid, lactose, dicalcium phosphate, Pluronic F-68 and sodium lauryl sulfate are admixed.

After sieving through a No. 60 screen, the mixture is granulated by wet process using an alcoholic solution containing polyvinylpyrrolidone, Carbowax 1500 and Carbowax 6000. When necessary, alcohol is added to make the powder into a paste-like mass. Then, corn starch is added and the blending is continued until uniform granules are formed. The mixture then is passed through a No. 10 screen, placed in a tray and dried in an oven maintained at 100° C. for 12 to 14 hours. The dried granules are sieved through a No. 16 screen, dry sodium lauryl sulfate and dry magnesium stearate are added thereto and blended. The mixture is compressed to a desired size and shape using a tableting machine.

The above cores are treated with a varnish and dusted with talc for preventing absorption of moisture and then provided with an undercoat layer. Varnish coating is repeated as many times as sufficient for internal use. The tablets are rendered completely round and smooth by application of a further undercoat layer and a smooth coating. Coloring coating is conducted until a desired coloring is obtained. After drying, the coated tablets are polished to give uniformly polished tablets.

EXAMPLE 14

| | |
|---|---|
| 2-(3,5-dimethyl-4-methoxy-2-pyridyl)methylsulfinyl-5-phenyl-1,3,4-oxadiazole | 5 g |
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 10.0 ml |

The above parabens, sodium metabisulfite and sodium chloride are dissolved in about half the above-specified volume of distilled water at 80° C. with stirring. The solution obtained is cooled to 40° C. The active ingredient of the invention is dissolved in said solution and then polyethylene glycol and polyoxyethylene sorbitan monooleate are dissolved therein. The remaining portion of distilled water for injection is added to the solution to make the final volume and the resulting solution is sterilized by filtration using an appropriate filter paper to give an injectable solution.

EXAMPLE 15

The following protocol was used for the Concanavalin A (ConA)-induced liver injury in mice. C57BL/6 mice were used. A solution of ConA (Sigma)in PBS was prepared at a concentration of 1.5 mg/ml. The mice were administered, i.p., with 200 ml of a 10% DMSO solution containing varying amounts (adjusted to give 25 mg/kg to 50 mg/kg of compound) of the representative compounds of interest. Fifteen minutes later, the mice were treated via the tail vein with 15 mg/kg of ConA in PBS along with 200 ml of 10% DMSO solution.

The mice were sacrificed after 17 hours and the blood collected into small conical tubes. The tubes were centrifuged and the serum collected and assayed for serum glutamic oxaloacetic transaminase (SGOT) (Sigma GOT kit). The high level enzyme standard (Sigma) was used to make the standard curve, as 100(undiluted), 50, 25, 12.5 and 0 S-F units/ml. Samples were diluted 1:5, 1:25 and 1:125 by adding 25 µl of serum to 100 µl of $H_2O$ and serially diluting 25 µl into 100 µl two more times. Then 100 µl of the Sigma substrate were added to each tube along with 20 µl of each diluted sample and enzyme standard. The tube was incubated in a 37° C. bath with gentle shaking for 1 hour. To that was added 100 ° C. of colorizing reagent and the tube was left to stand for 30 minutes. Then 500 µl of 0.8N NaOH solution were added, the tubes were capped and inverted to mix thoroughly. A 150 µl aliquot of each sample and 150 µl of the standard were added to wells of a 96-well plate and color formation was monitored at 490 nm. The amounts of SGOT were calculated using a standard curve, converted to Sigma-Frankel units/ml.

TABLE 5

| Compound | SGOT (% decrease) | Dosage (mg/kg) (i.p.) |
|---|---|---|
| 16 | 85 | 50 |
| 19 | 87 | 50 |
| 35 | 45 | 50 |
| 44 | 86 | 25 |
| 48 | 51 | 50 |
| 60 | 60 | 50 |
| 67 | 55 | 50 |
| 69 | 30 | 50 |
| 70 | 82 | 50 |
| 89 | 95 | 50 |
| 97 | 45 | 20 |
| 101 | 68 | 50 |
| 113 | 80 | 50 |

All references cited herein are herein incorporated by reference in entirety.

While the invention has been described in detail and with reference to certain embodiments thereof, it would be apparent to one skilled in the art that various changes and modifications can be made without departing from the spirit and scope thereof.

We claim:

1. A 1,3,4-oxadiazole of the formula:

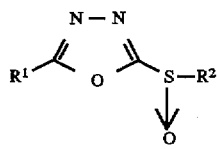

wherein $R^1$ is an alkyl group, a phenyl group optionally having a lower alkoxy group, a hydroxy group, a lower alkyl group, optionally having a halogen substituent, a halogen atom or an anilino group, optionally substituted on the phenyl ring with 1–3 lower alkyl groups optionally having a halogen substituent or a halogen atom, an adamantyl group, a naphthyl group, a phenyl(lower)alkyl group, optionally having a phenoxy group as a substituent on the phenyl ring, or an unsaturated 5-membered to 11-membered heteromonocyclic or heterobicyclic group having 1–4 heteroatoms selected from the group consisting of a nitrogen, an oxygen and a sulfur atom, said heterocyclic group being optionally substituted with a phenyl group, a phenoxy group or a lower alkyl group; R² is a phenyl group, optionally having 1–3 lower alkyl groups or hydroxyl groups, a phenyl (lower)alkyl group,

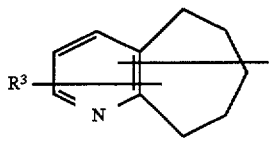

wherein R³ is a hydrogen atom, or a lower alkoxy group, a quinolyl group or a lower alkyl group substituted by an unsaturated 5-membered to 11-membered heteromonocyclic or heterobicyclic group having 1–4 heteroatoms selected from the group consisting of a nitrogen, an oxygen and a sulfur atom, said heterocyclic group being optionally substituted with a phenyl group having optionally a lower alkyl substituent on the phenyl ring, a phenyl(lower)alkyl group, a lower alkoxy group, an oxo group, a lower alkyl group or a phenoxy group and n is 0 or 1; with the provisos that R¹ is not a 4H-pyranyl group or a 1,4-dihydropyridyl group; when R¹ is a lower alkyl group or phenyl group, R² is not a pyrazyl-substituted lower alkyl group having a lower alkyl group, a lower alkoxy group or an oxo group; and R² is not a 1,1,3-trioxo-1,2-benzisothiazolylmethyl group; or a salt thereof.

2. The 1,3,4-oxadiazole, or salt thereof, of claim 1, wherein R¹ is an alkyl group and R² is a phenyl(lower)alkyl group.

3. The 1,3,4-oxadiazole, or salt thereof, of claim 1, wherein R¹ is an alkyl group and R² is

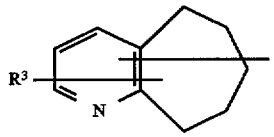

wherein R³ is a hydrogen atom or a lower alkoxy group.

4. The 1,3,4-oxadiazole, or salt thereof, of claim 1, wherein R¹ is an alkyl group and R² is a lower alkyl group substituted with an unsaturated 5-membered to 11-membered heteromonocyclic or heterobicyclic group having 1–4 heteroatoms selected from the group consisting of a nitrogen, an oxygen and a sulfur atom, said heterocyclic group being optionally substituted with a phenyl group optionally having a lower alkyl substituent on the phenyl ring, a phenyl(lower)alkyl group, a lower alkoxy group, an oxo group, a lower alkyl group or a phenoxy group.

5. The 1,3,4-oxadiazole, or salt thereof, of claim 1, wherein R¹ is an alkyl group and R² is a phenyl group, optionally having 1–3 lower alkyl groups or hydroxyl groups, or a quinolyl group.

6. The 1,3,4-oxadiazole, or salt thereof, of claim 1, wherein R¹ is an unsaturated 5-membered to 11-membered heteromonocyclic or heterobicyclic group having 1–4 heteroatoms selected from the group consisting of a nitrogen, an oxygen and a sulfur atom, said heterocyclic group being optionally substituted with a phenyl group, a phenoxy group or a lower alkyl group and R² is a phenyl(lower)alkyl group.

7. The 1,3,4-oxadiazole, or salt thereof, of claim 1, wherein R¹ is an unsaturated 5-membered to 11-membered heteromonocyclic or heterobicyclic group having 1–4 heteroatoms selected from the group consisting of a nitrogen, an oxygen and a sulfur atom, said heterocyclic group being optionally substituted with a phenyl group, a phenoxy group or a lower alkyl group; and R² is

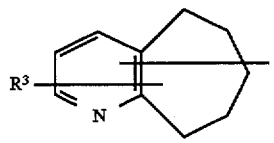

wherein R³ is a hydrogen atom or a lower alkoxy group.

8. The 1,3,4-oxadiazole, or salt thereof, of claim 1, wherein R¹ is an unsaturated 5-membered to 11-membered heteromonocyclic or heterobicyclic group having 1–4 heteroatoms selected from the group consisting of a nitrogen, an oxygen and a sulfur atom, said heterocyclic group being optionally substituted with a phenyl group, a phenoxy group or a lower alkyl group and R² is a lower alkyl group substituted with an unsaturated 5-membered to 11-membered heteromonocyclic or heterodicyclic group having 1–4 heteroatoms selected from the group consisting of a nitrogen, an oxygen and a sulfur atom, said heterocyclic group being optionally substituted with a phenyl group, optionally having a lower alkyl substituent on the phenyl ring, a phenyl(lower)alkyl group, a lower alkoxy group, an oxo group, a lower alkyl group or a phenoxy group.

9. The 1,3,4-oxadiazole, or salt thereof, of claim 1, wherein R¹ is an unsaturated 5-membered to 11-membered heteromonocyclic or heterobicyclic group having 1–4 heteroatoms selected from the group consisting of a nitrogen, an oxygen and a sulfur atom, said heterocyclic group being optionally substituted with a phenyl group, a phenoxy group or a lower alkyl group and R² is a phenyl group, optionally having 1–3 lower alkyl groups or hydroxyl groups, or a quinolyl group.

10. The 1,3,4-oxadiazole, or salt thereof, of claim 1, wherein R¹ is a phenyl group optionally having a lower alkoxy group, a hydroxy group, a lower alkyl group, optionally having a halogen substituent, a halogen atom or an anilino group, optionally substituted on the phenyl ring by 1–3 lower alkyl groups, optionally having a halogen substituent, or halogen atoms, an adamantyl group, a naphthyl group or a phenyl(lower)alkyl group, optionally having a phenoxy group as a substituent on the phenyl ring.

11. The 1,3,4-oxadiazole, or salt thereof, of claim 1, which is 2-methyl-5-(3,5-dimethyl-4-methoxy-2-pyridyl) methylsulfinyl-1,3,4-oxadiazole.

12. An immunosuppressant comprising the 1,3,4-oxadiazole, or salt thereof, of claim 1 in combination with a pharmaceutically acceptable carrier.

13. An anti-inflammatory composition comprising the 1,3,4-oxadiazole, or salt thereof, of claim 1 in combination with a pharmaceutically acceptable carrier.

* * * * *